United States Patent
Zocca et al.

(10) Patent No.: US 7,331,346 B2
(45) Date of Patent: **\*Feb. 19, 2008**

(54) MONITORING AND CONTROL FOR A LARYNGEAL MASK AIRWAY DEVICE

(75) Inventors: Mario Zocca, Verona (IT); Archibald I. J. Brain, Longcross Chertsey (GB); Paolo Mozzo, Verona (IT)

(73) Assignee: Indian Ocean Medical, Inc., Mahe (SC)

( * ) Notice: Subject to any disclaimer, the term of this patent is extended or adjusted under 35 U.S.C. 154(b) by 0 days.

This patent is subject to a terminal disclaimer.

(21) Appl. No.: 10/347,036

(22) Filed: Jan. 17, 2003

(65) Prior Publication Data

US 2003/0172925 A1  Sep. 18, 2003

Related U.S. Application Data

(63) Continuation of application No. 09/612,059, filed on Jul. 7, 2000, now abandoned, which is a continuation-in-part of application No. 09/382,030, filed on Aug. 24, 1999, now abandoned, and a continuation-in-part of application No. 09/602,264, filed on Jun. 23, 2000, now abandoned.

(30) Foreign Application Priority Data

Dec. 24, 1997 (GB) .................................. 9727367.6
Dec. 21, 1998 (WO) ..................... PCT/GB98/03849

(51) Int. Cl.
*A61M 16/00* (2006.01)
(52) U.S. Cl. ............................ 128/207.14; 128/207.15
(58) Field of Classification Search ........... 128/200.26, 128/201.28, 202.22, 204.18, 204.29, 205.23; 604/96, 100

See application file for complete search history.

(56) References Cited

U.S. PATENT DOCUMENTS 2,862,498 A    12/1958    Weekes (Continued)

FOREIGN PATENT DOCUMENTS

CA    2067782    6/1999

(Continued)

OTHER PUBLICATIONS

Brain, "The laryngeal mask airway -a possible new solution to airway problems in the emergency situation," *Archives of Emergency Medicine*, 1984, 1, 229-232.

(Continued)

*Primary Examiner*—Michael J. Hayes
*Assistant Examiner*—Michael Mendoza
(74) *Attorney, Agent, or Firm*—Wilmer Cutler Pickering Hale and Dorr LLP

(57) ABSTRACT

The disclosed method of monitoring the cuff pressure of an LMA provides an estimation of a patient's anesthetic state. Cuff pressure tends to rise and fall during IPPV and spontaneous breathing. One of the disclosed methods activates an alarm if an instantaneous value of the cuff pressure exceeds selected levels. This method may also automatically adjust the selected levels. One of the disclosed methods activates an alarm if activity of the cuff pressure as observed over a period of time exceeds a selected level.

15 Claims, 22 Drawing Sheets

U.S. PATENT DOCUMENTS

| | | |
|---|---|---|
| 3,529,596 A | 9/1970 | Garner |
| 3,554,673 A | 1/1971 | Schwartz et al. |
| 3,683,908 A | 8/1972 | Michael et al. |
| 3,794,036 A | 2/1974 | Carroll |
| 3,931,822 A * | 1/1976 | Marici ................... 128/207.15 |
| 4,067,329 A * | 1/1978 | Winicki ................. 128/202.22 |
| 4,104,357 A | 8/1978 | Blair |
| 4,116,201 A | 9/1978 | Shah |
| 4,134,407 A | 1/1979 | Elam |
| 4,159,722 A | 7/1979 | Walker |
| 4,178,938 A | 12/1979 | Au |
| 4,178,940 A | 12/1979 | Au |
| 4,231,365 A | 11/1980 | Scarberry |
| 4,256,099 A | 3/1981 | Dryden |
| 4,285,340 A | 8/1981 | Gesari et al. |
| 4,471,775 A | 9/1984 | Clair et al. |
| 4,501,273 A | 2/1985 | McGinnis |
| 4,509,514 A | 4/1985 | Brain |
| 4,510,273 A | 4/1985 | Miura et al. |
| 4,526,196 A | 7/1985 | Pistillo |
| 4,553,540 A | 11/1985 | Straith |
| 4,583,917 A | 4/1986 | Shah |
| 4,630,606 A | 12/1986 | Weerda et al. |
| 4,689,041 A | 8/1987 | Corday et al. |
| 4,700,700 A | 10/1987 | Eliachar |
| 4,770,170 A | 9/1988 | Sato et al. |
| 4,793,327 A | 12/1988 | Frankel |
| 4,825,862 A | 5/1989 | Sato et al. |
| 4,832,020 A | 5/1989 | Augustine |
| 4,850,349 A | 7/1989 | Farahany |
| 4,856,510 A | 8/1989 | Kowalewski |
| 4,872,483 A | 10/1989 | Shah |
| 4,924,862 A | 5/1990 | Levinson |
| 4,953,547 A | 9/1990 | Poole, Jr. |
| 4,981,470 A | 1/1991 | Bombeck, IV |
| 4,995,388 A | 2/1991 | Brain |
| 5,038,766 A | 8/1991 | Parker |
| 5,042,469 A | 8/1991 | Augustine |
| 5,042,476 A | 8/1991 | Smith |
| 5,203,320 A | 4/1993 | Augustine |
| 5,218,970 A | 6/1993 | Turnbull et al. |
| 5,235,973 A | 8/1993 | Levinson |
| 5,241,956 A | 9/1993 | Brain |
| 5,249,571 A | 10/1993 | Brain |
| 5,273,537 A | 12/1993 | Haskvitz |
| 5,277,178 A | 1/1994 | Dingley et al. |
| 5,282,464 A | 2/1994 | Brain |
| 5,297,547 A | 3/1994 | Brain |
| 5,303,697 A | 4/1994 | Brain |
| 5,305,743 A | 4/1994 | Brain |
| 5,311,861 A | 5/1994 | Miller et al. |
| 5,331,967 A | 7/1994 | Akerson |
| 5,339,805 A | 8/1994 | Parker |
| 5,339,808 A | 8/1994 | Michael |
| 5,355,879 A | 10/1994 | Brain |
| 5,361,753 A | 11/1994 | Pothman et al. |
| 5,391,248 A | 2/1995 | Brain |
| 5,400,771 A * | 3/1995 | Pirak et al. ................. 600/109 |
| 5,421,325 A * | 6/1995 | Cinberg et al. ........ 128/200.26 |
| 5,452,715 A | 9/1995 | Boussignac |
| 5,459,700 A | 10/1995 | Jacopb |
| 5,487,383 A * | 1/1996 | Levinson ............... 128/207.15 |
| 5,529,582 A | 6/1996 | Fukuhara |
| 5,546,935 A | 8/1996 | Champeau |
| 5,546,936 A | 8/1996 | Virag et al. |
| 5,551,420 A | 9/1996 | Lurie et al. |
| 5,554,673 A | 9/1996 | Shah |
| 5,569,219 A | 10/1996 | Hakki et al. |
| 5,577,693 A | 11/1996 | Corn |
| 5,582,167 A * | 12/1996 | Joseph ................... 128/207.15 |
| 5,584,290 A | 12/1996 | Brain |
| 5,599,301 A | 2/1997 | Jacobs et al. |
| 5,623,921 A | 4/1997 | Kinsinger et al. |
| 5,626,151 A | 5/1997 | Linden |
| 5,632,271 A | 5/1997 | Brain |
| RE35,531 E | 6/1997 | Callaghan et al. |
| 5,653,229 A | 8/1997 | Greenberg |
| 5,655,528 A | 8/1997 | Pagan |
| 5,682,880 A | 11/1997 | Brain |
| 5,692,498 A | 12/1997 | Lurie et al. |
| 5,694,929 A | 12/1997 | Christopher |
| 5,711,293 A | 1/1998 | Brain |
| 5,738,094 A | 4/1998 | Hoftman |
| 5,743,254 A | 4/1998 | Parker |
| 5,743,258 A * | 4/1998 | Sato et al. ............. 128/207.15 |
| 5,746,202 A | 5/1998 | Pagan |
| 5,771,889 A | 6/1998 | Pagan |
| 5,778,872 A | 7/1998 | Fukunaga et al. |
| 5,791,341 A | 8/1998 | Bullard |
| 5,816,240 A | 10/1998 | Komesaroff |
| 5,819,723 A | 10/1998 | Joseph |
| 5,832,916 A * | 11/1998 | Lundberg ............... 128/202.22 |
| 5,850,832 A | 12/1998 | Chu |
| 5,855,203 A | 1/1999 | Matter |
| 5,856,510 A | 1/1999 | Meng et al. |
| 5,860,418 A | 1/1999 | Lundberg |
| 5,865,176 A | 2/1999 | O'Neil |
| 5,878,745 A | 3/1999 | Brain |
| 5,881,726 A | 3/1999 | Neame |
| 5,896,858 A | 4/1999 | Brain |
| 5,915,383 A | 6/1999 | Pagan |
| 5,924,862 A | 7/1999 | White |
| 5,937,860 A | 8/1999 | Cook |
| 5,957,133 A * | 9/1999 | Hart ....................... 128/207.14 |
| 5,979,445 A | 11/1999 | Neame et al. |
| 5,983,891 A | 11/1999 | Fukunaga |
| 5,983,894 A | 11/1999 | Fukunaga et al. |
| 5,983,896 A | 11/1999 | Fukunaga et al. |
| 5,983,897 A | 11/1999 | Pagan |
| 5,988,167 A | 11/1999 | Kamen |
| 5,996,582 A | 12/1999 | Turnbull |
| 6,003,510 A | 12/1999 | Anunta |
| 6,003,511 A | 12/1999 | Fukunaga et al. |
| 6,003,514 A | 12/1999 | Pagan |
| 6,012,452 A | 1/2000 | Pagan |
| 6,021,779 A | 2/2000 | Pagan |
| 6,050,264 A | 4/2000 | Greenfield |
| 6,062,219 A | 5/2000 | Lurie et al. |
| 6,070,581 A | 6/2000 | Augustine et al. |
| 6,079,409 A | 6/2000 | Brain |
| D429,811 S | 8/2000 | Bermudez |
| 6,095,144 A | 8/2000 | Pagan |
| 6,098,621 A | 8/2000 | Esnouf et al. |
| 6,110,143 A | 8/2000 | Kamen |
| 6,116,243 A | 9/2000 | Pagan |
| 6,119,695 A | 9/2000 | Augustine et al. |
| 6,131,571 A | 10/2000 | Lampotang et al. |
| 6,149,603 A * | 11/2000 | Parker ........................ 600/532 |
| 6,155,257 A | 12/2000 | Lurie et al. |
| 6,213,120 B1 | 4/2001 | Block et al. |
| 6,224,562 B1 | 5/2001 | Lurie et al. |
| 6,234,985 B1 | 5/2001 | Lurie et al. |
| 6,240,922 B1 | 6/2001 | Pagan |
| 6,251,093 B1 | 6/2001 | Valley et al. |
| 6,269,813 B1 | 8/2001 | Fitzgerald |
| 6,315,739 B1 | 11/2001 | Merilainen et al. |
| 6,390,093 B1 | 5/2002 | Mongeon |
| 6,427,686 B2 | 8/2002 | Augustine et al. |
| 6,439,232 B1 | 8/2002 | Brain |
| 6,450,164 B1 | 9/2002 | Banner et al. |
| 6,631,720 B1 | 10/2003 | Brain et al. |
| 6,647,984 B1 | 11/2003 | O'Dea et al. |
| 6,651,666 B1 | 11/2003 | Owens |
| 6,705,318 B1 | 3/2004 | Brain |

| | | | |
|---|---|---|---|
| 7,004,169 B2 | 2/2006 | Brain et al. |
| 7,040,322 B2 | 5/2006 | Fortuna et al. |
| 7,051,096 B1 | 5/2006 | Krawiec et al. |
| 7,051,736 B2 | 5/2006 | Banner et al. |
| 7,096,868 B2 | 8/2006 | Tateo et al. |
| 7,097,802 B2 | 8/2006 | Brain et al. |
| 7,128,071 B2 | 10/2006 | Brain et al. |
| 7,134,431 B2 | 11/2006 | Brain et al. |
| 7,156,100 B1 | 1/2007 | Brain et al. |
| 7,159,589 B2 | 1/2007 | Brain |
| 2003/0051734 A1 | 3/2003 | Brain |
| 2003/0101998 A1 | 6/2003 | Zocca et al. |
| 2003/0131845 A1 | 7/2003 | Lin |
| 2003/0172925 A1 | 9/2003 | Zocca et al. |
| 2005/0274383 A1 | 12/2005 | Brain |
| 2006/0124132 A1 | 6/2006 | Brain |
| 2006/0254596 A1 | 11/2006 | Brain |

FOREIGN PATENT DOCUMENTS

| | | |
|---|---|---|
| CA | 2012750 | 8/1999 |
| DE | 10042172 | 4/2001 |
| EP | 0 389 272 | 9/1990 |
| EP | 0 402 872 | 12/1990 |
| EP | 0 294 200 | 4/1992 |
| EP | 0 580 385 | 5/1996 |
| EP | 0 712 638 | 5/1996 |
| EP | 0 732 116 | 9/1996 |
| EP | 0 796 631 | 9/1997 |
| EP | 0 845 276 | 6/1998 |
| EP | 0 865 798 | 9/1998 |
| EP | 0 922 465 | 6/1999 |
| EP | 1125595 | 1/2001 |
| EP | 1119386 B1 | 9/2005 |
| GB | 2111394 | 12/1982 |
| GB | 2205499 | 6/1987 |
| GB | 2298797 A | 9/1996 |
| GB | 2317342 | 8/1997 |
| GB | 2317830 | 9/1997 |
| GB | 2318735 | 10/1997 |
| GB | 2319478 | 10/1997 |
| GB | 2321854 | 1/1998 |
| GB | 2323289 | 2/1998 |
| GB | 2323290 | 3/1998 |
| GB | 2323291 | 3/1998 |
| GB | 2323292 | 3/1998 |
| GB | 2359996 | 1/2001 |
| GB | 2359996 | 9/2001 |
| JP | 10118182 | 5/1998 |
| JP | 10216233 | 8/1998 |
| JP | 10263086 | 10/1998 |
| JP | 10277156 | 10/1998 |
| JP | 10314308 | 12/1998 |
| JP | 10323391 | 12/1998 |
| JP | 10328303 | 12/1998 |
| JP | 11128349 | 5/1999 |
| JP | 11192304 | 7/1999 |
| JP | 11206885 | 8/1999 |
| WO | WO 91/03207 | 3/1991 |
| WO | WO 91/07201 | 5/1991 |
| WO | WO-91/12845 | 9/1991 |
| WO | WO 91/12845 | 9/1991 |
| WO | WO 92/13587 | 8/1992 |
| WO | WO 95/33506 | 12/1995 |
| WO | WO 97/12640 | 4/1997 |
| WO | WO 97/12641 | 4/1997 |
| WO | WO 98/16273 | 4/1998 |
| WO | WO 99/06093 | 2/1999 |
| WO | WO-00/09189 | 2/2000 |
| WO | WO 00/22985 | 4/2000 |
| WO | WO 00/23135 | 4/2000 |
| WO | WO 00/61212 | 10/2000 |

OTHER PUBLICATIONS

Brain, "The laryngeal mask airway," *Anaesthesia*, 1985, vol. 40, pp. 356-361.

Brain, "Three cases of difficult intubation overcome by the laryngeal mask airway," *Anaesthesia*, 1985, vol. 40, pp. 353-355.

DeMello, et al., "The use of the laryngeal mask airway in primary anaesthesia," *Anaesth. Corresp.* (1990) 45,9:793.

Hickey, et al., "Cardiovascular response to insertion of Brain's laryngeal mask," *Anaesthesia* 1990, vol. 45, pp. 629-633.

Davies, et al., "Laryngeal mask airway and tracheal tube insertion by unskilled personnel," *The Lancet*, vol. 336, pp. 977-979.

Brain, "The Laryngeal Mask-A New Concept in Airway Management," *Br. J.Anaesth.*, (1983), 55, 801-805.

Brodrick et al., "The laryngeal mask airway," *Anaesthesia*, 1989, vol. 44, pp. 238-241.

Inomata, et al., "Transient Bilateral Vocal Cord Paralysis after Insertion of a Laryngeal Mask Airway," *Anesthesiology*, 82:787-788, 1995.

Majumder, et al., "Bilateral Lingual nerve Injury following the use of the laryngeal mask airway," *Anaesthesia*, 1998, 53, pp. 184-186.

Wynn, et al., "Tongue Cyanosis after Laryngeal Mask Airway Insertion," *Anesthesiology*, V. 80, No. 6, Jun. 1994, p. 1403.

Nagai, "Unilateral hypoglossal nerve paralysis following the use of the laryngeal mask airway," *Anaesthesia*, 1994, vol. 49, pp. 603-604.

Brain, et al., "A new laryngeal mask prototype," *Anaesthesia*, 1995, vol. 50, pp. 42-48.

Burgard, et al., The Effect of Laryngeal Mask Cuff Pressure on Postoperative Sore Throat Incidence, *J. of Clinical Anesthesia* 8:198-201, 1996.

Benumof, "Laryngeal Mask Airway and the ASA Difficult Airway Algorithm," *Anesthesiology* 1996:v84 No. 3:686-99.

Pennant, "Comparison of the Endotracheal Tube and Laryngeal Mask in Airway Management by Paramedical Personnel," *Anesth Analg* 1992:74:531-4.

Brimacombe, "The split laryngeal mask airway," p. 639.

Worthington, et al., "Proceedings of the Anaesthetic Research Society," *Br. J. of Anaesthesia* 1995 75:228P-229P.

Heath, "Endotracheal intubation through the Laryngeal Mask—helpful when laryngoscopy is difficult or dangerous," *European Journal of Anaesthesiology* 1991, Suppl. 4, 41-45.

Kambic, et al., "Intubation Lesions of the Larynx," *Br. J. Anasth.* 1978, 50, 587-590.

Abdelatti, "A cuff pressure controller for tracheal tubes and laryngeal mask airway," *Anaesthesia*, 1999, 54 pp. 981-986.

Muthuswamy, et al., "The Use of Fuzzy Integrals and Bispectral Analysis of the Electroencephalogram to Predict Movement Under Anesthesia," *IEEE Transactions on Biomedical Engineering*, vol. 46, No. 3, Mar. 1999, pp. 290-299.

Glen, "The development of 'Diprifusor': a TCI system for propofol," *Anaesthesia* 1998, 53, Suppl. 1, pp. 13-21.

Gray et al., "Development of the technology for 'Diprifusor' TCI systems," *Anaesthesia* 1998, 53, Suppl. 1, pp. 22-27.

Engbers, "Practical use of 'Diprifusor' systems", *Anaesthesia* 1998, 53, Suppl. 1, pp. 28-34.

Doyle et al., "Intraoperative Awareness: A Continuing Clinical Problem," http://doyle.ibme.utoronto.ca/anesthesia/aware.htm.

Eriksson, et al., "Functional Assessment of the Pharynx at Rest and during Swallowing in Partially Paralyzed Humans," *Anesthesiology* vol. 87, No. 5, Nov. 1997, pp. 1035-1042.

Cuff-Pressure-Control CDR 2000, LogoMed.

Seegobin, et al., "Endotracheal cuff pressure and tracheal mucosal blood flow: endoscopic study of effects of four large volume cuffs," *British Medical Journal*, vol. 288, Mar. 31, 1984.

Raeder, et al., "Tracheal tube cuff pressures," *Anaesthesia*, 1985, vol. 40, pp. 444-447.

Jacobson et al., A Study of Intracuff Pressure Measurements, Trends and Behaviours in Patients During Prolonged Periods of Tracheal Intubation, *Br. J. Anaesth.* 1981, 53, 97.

Willis, et al., "Tracheal tube cuff pressure," *Anaesthesia*, 1988, vol. 43, pp. 312-314.

Miller, "A pressure regulator for the cuff of a tracheal tube," *Anaesthesia*, 1992, vol. 47, pp. 594-596.

Patel, et al, "Trachael tube cuff pressure," *Anaesthesia*, 1984, vol. 39, pp. 862-864.

Pippin, et al., "Long-term tracheal intubation practice in the United Kingdom", *Anaesthesia*, 1983, vol. 38, pp. 791-795.

Bernhard, et al., "Adjustment of Intracuff Pressure to Prevent Aspiration," *Anesthesiology* v. 50 No. 4:363-366, 1979.

Bernhard, et al., "Physical Characteristics of and Rates of Nitrous Oxide Diffusion into Tracheal Tube Cuffs," *Anesthesiology* 48:413-417 1978.

Craven, "Prevention of Hospital-Acquired Pneumonia: Measuring Effect in Ounces, Pounds, and Tons, "*Annals of Internal Medicine*, vol. 122, No. 3, pp. 229-231 Feb. 1, 1995.

Lindholm, "Prolonged Endotracheal Intubation," *ACTA Anaesthesiologica Scandinavica* 1969 vol. 33 32-46.

Rieger et al.; *Anesthesiology*, V 87, No. 1; Jul. 1997.

Laryngeal Mask Publications; Dec. 1998; http://www.saga.nl/lmapubl.htm.

"Improving Anesthesia"; *MedPro Month*; Nov.-Dec. 1997; pp. 311-312.

"Neurometric Assessment of Adequacy of Intraoperative Anesthetic"; Mar. 1999; http://www.pnl.gov/medical/info/neuro.htm.

International Search Report; WO99/33508 (PCT/GB98/03849).

Martin, Todd, "Patentability of Methods of Medical Treatment: A Comparative Study," Jun. 200, pp. 381-423.

Caplan et al., "Adverse Respiratory Events in Anesthesia: A Closed Claims Analysis", Anesthesiology, 72:828-833, 1990.

Communication of a notice of opposition, European Patent Office, Feb. 15, 2006 (cover page and pp. 1-4).

Kapila, A., et al., "Intubating LMA: A Preliminary Assessment of Performance", British Journal of Anesthesia, 1995, 75:228-229 (Abstract).

Observations by Third Party Concerning European Patent Application No. 99 947 765.6-2318, European Patent Office, Munich, Germany, Jan. 18, 2005 (3 pgs.).

Response to Complaint Matter No. 4b 0 440-05, In the Matter of: LMA Deutschland GmbH versus Ambu (Deutschland) GmbH, Feb. 10, 2006, pp. 1-47.

* cited by examiner

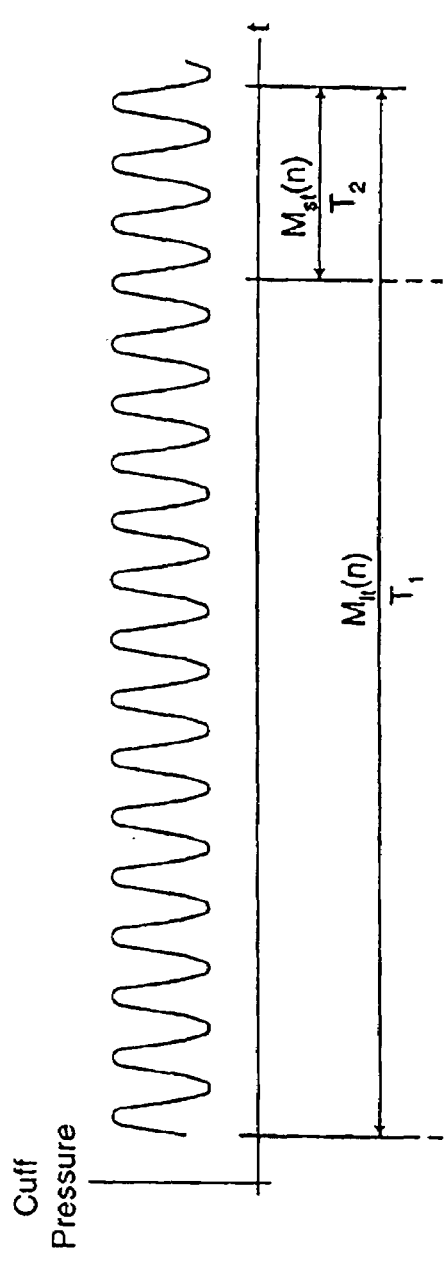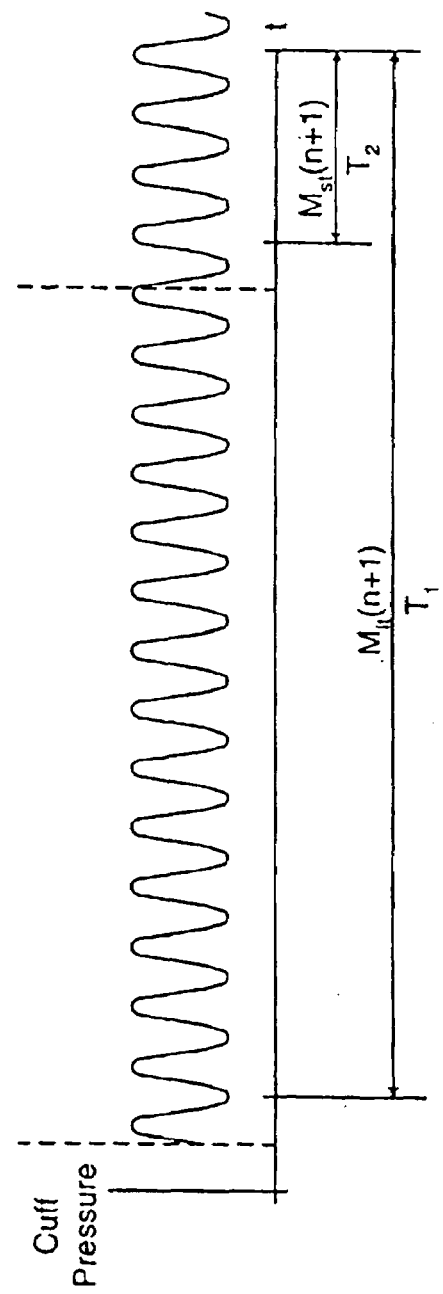
FIG. 6A
FIG. 6B

MONITORING AND CONTROL FOR A LARYNGEAL MASK AIRWAY DEVICE

REFERENCE TO RELATED APPLICATIONS

This application is a continuation of U.S. patent application Ser. No. 09/612,059 filed Jul. 7, 2000, now abandoned which is a continuation-in-part of U.S. patent application Ser. No. 09/602,264, filed Jun. 23, 2000, now abandoned and a continuation-in-part of U.S. patent application Ser. No. 09/382,030, filed Aug. 24, 1999 now abandoned.

BACKGROUND OF THE INVENTION

The present invention relates to monitoring patients during surgical procedures in which a general anesthetic has been applied. More specifically, the present invention relates to methods and apparatus for automatically generating an alarm when a patient's depth of anesthesia is insufficient for the surgical procedure being performed.

One important function performed by anesthesiologists relates to maintaining an open airway for a patient throughout a surgical procedure. When a general anesthetic is applied, some type of artificial airway is almost always established for the patient. One popular device for establishing an artificial airway is an endotracheal tube. Another is the well known laryngeal mask airway (LMA).

FIG. 1 shows a perspective view of a prior art LMA 100 and FIG. 2 illustrates an LMA 100 that has been inserted into a patient. LMAs such as LMA 100 are described for example in U.S. Pat. No. 4,509,514. LMA 100 includes an airway tube 110 and a mask portion 130. The mask portion 130 includes a generally elliptical inflatable cuff 134. The tube 110 and mask portion 130 are coupled together and define a continuous, sealed, airway extending from a proximal end 112 of tube 110 to an opening 136 defined in the mask portion 130. LMA 100 also includes an inflation tube 138 for selectively inflating or deflating cuff 134.

In operation, the cuff 134 is initially deflated, and then the mask portion is inserted through the patient's mouth into the patient's pharynx, while the proximal ends of the tube 110 and of the inflation tube 138 remain outside the patient. The mask portion is preferably positioned so that the distal end 140 of cuff 134 rests against the patient's normally closed esophagus and so that the open end 136 is aligned with the entryway of the patient's trachea (i.e., the patient's glottic opening). After the mask portion is so positioned, the cuff is inflated thereby forming a seal around the patient's glottic opening and this establishes a sealed airway extending from the proximal end 112 of the tube 110 to the patient's trachea.

For convenience of exposition, the term "fully inserted configuration" shall be used herein to refer to an LMA that has been inserted into a patient and has the following characteristics: (1) the mask portion is disposed around the patient's glottic opening; (2) the cuff is inflated forming a seal around the patient's glottic opening; (3) the distal tip of the cuff is disposed adjacent the esophageal sphincter; (4) the proximal end of the tube 110 is disposed outside of the patient so that the LMA defines a sealed airway extending from outside the patient's mouth to the patient's lungs (the airway extending from the proximal end 112 of tube 110 to the opening 136 of the mask portion); and (5) the proximal end of the inflation tube remains outside the patient's mouth. FIG. 2 shows an LMA in the fully inserted configuration.

The following steps are normally performed when using an LMA to establish an airway in a patient for use during a surgical procedure. Initially, the patient is anesthetized to a depth that is sufficiently deep for permitting LMA insertion. This process is called induction of anesthesia and is normally accomplished by giving the patient an intravenous injection. The depth of anesthesia required for LMA insertion is less than the depth required for insertion of an endotracheal tube (since the endotracheal tube must pass through the vocal cords, whereas an LMA does not). An LMA is then inserted into the patient and once inserted the anesthesiologist preferably confirms that the LMA has been properly positioned in the fully inserted configuration (e.g., the anesthesiologist preferably confirms that the inflated cuff has formed a seal around the patient's glottic opening). Such checking can be performed by (1) noting whether the patient's chest rises when the anesthesia gas reservoir bag is squeezed and (2) checking for the presence of carbon dioxide in the expired gas and measuring the oxygen saturation. After proper placement of the LMA has been confirmed, the proximal end 112 of the tube 110 may be coupled to a ventilation machine that applies intermittent positive pressure ventilation (IPPV) to the patient and ventilates the patient with a mix of gasses including (1) oxygen; (2) nitrous oxide; and (3) an anesthetic agent. Alternatively, the type of surgery being performed may permit the patient to breathe spontaneously via the LMA during the procedure. After conclusion of the surgical procedure, the LMA is normally removed shortly after the patient becomes responsive to verbal stimulus and can open their mouth when requested to do so.

In addition to establishing and monitoring the patient's airway, another important function performed by anesthesiologists relates to determining the amount of anesthetic drugs to be administered to the patient during a surgical procedure. Briefly, three competing goals for administration of anesthetic drugs during surgical procedures are (1) to induce a level of anesthesia that is "sufficiently deep" so that the patient experiences no pain and remains completely unaware during the surgical procedure; (2) to avoid overmedicating the patient; and (3) to optimize the recovery time. The term "depth of anesthesia" is difficult to define, since it relates to a sleep-like state which is not yet understood in physiological terms. Anesthesiologists nonetheless appreciate when anesthesia is sufficiently deep to meet the needs of preventing reflex response to a surgical incision, since when the level of anesthesia is less than this somewhat elusive threshold the patient will visibly move. Obviously it is undesirable to induce a level of anesthesia that is equal to or less than this threshold and experienced anesthesiologists learn how to keep the majority of their patients sufficiently deeply anesthetized to prevent (1) interference with the course of the procedure due to patient movement and (2) suffering due to the patient regaining consciousness sufficiently to experience pain.

Anesthesia may be General or Local, the former term meaning that unconsciousness is induced, while in the latter a lack of sensation is produced pharmacologically in a specific area of the body. Often, a combination of the two techniques is used, so as to reduce the total amount of general anesthesia required to maintain unconsciousness. This is especially desirable in patients whose condition might be made worse by side-effects of the general anesthetic agents used, for example patients with severe cardiac or pulmonary disease. Often, patients are paralyzed as well as anesthetized. This prevents movement and again reduces the amount of general anesthesia required.

Unfortunately, it is difficult to precisely tailor the drug requirements to maintain a desired level of anesthesia because (1) patients' responses to drugs vary and (2) there is no precise way of measuring anesthetic depth. Hence, patients sometimes recover sufficient consciousness during surgical procedures to experience pain. For example, when seriously ill patients are given minimal amounts of anesthetic drugs to prevent worsening of their underlying condition, and are also paralyzed, it is very difficult to determine their level of awareness.

One way to prevent patients from recalling awareness after a surgical procedure is to administer drugs which suppress short-term memory. Such drugs are highly effective, but when they are given after an episode of awareness has occurred, the actual time during which the patient is aware may cause enormous distress and this is not only undesirable on humanitarian grounds, but may potentially worsen the state of a seriously ill patient.

The practice of anesthesiology is thus a balancing act, in which too much or too little anesthesia may lead to serious or fatal outcomes, quite apart from the risks inherent in the surgical procedure itself. A method of judging anesthetic depth with a degree of precision is therefore highly desirable and it is not surprising that a number of different approaches have been made attempting to solve the problem.

One method relies on observing changes in the patient's cerebral activity as seen on the electro-encephalogram (EEG) while applying auditory stimuli. A more recent method attempts to generate a simple numeric score indicative of the depth of anesthesia by analyzing the patient's complex EEG waveforms. Yet another method detects facial muscle activity and attempts to relate this to pain sensation. Attempts have also been made to relate the activity of the esophageal muscles to depth of anesthesia, but no clear relationship has been found and this method has been abandoned. Some or all of these methods may be combined with information from changes in blood pressure, pulse rate and respiratory rate or depth. An indicator known as the Bispectral Index, or "BIS", which gives a single number relating to awareness based on EEG analysis, is currently the most popular automatically generated indicator of anesthetic depth.

While these prior art methods may be useful, it would be advantageous to develop other methods and apparatus for estimating a patient's level of anesthesia and in particular for doing so during surgical procedures in which an LMA is used to establish or clear a patient's airway.

SUMMARY OF THE INVENTION

The larynx and pharynx form part of the upper airway through which gases are drawn in and out of the lungs. The human larynx, which houses the vocal cords, is situated in the neck where it forms an opening in the front wall of the pharynx. The pharynx defines a generally flattened conical tube whose walls are formed from three sets of diagonally-running muscles known as the pharyngeal constrictor muscles. These muscles are attached to the larynx and together with other laryngeal muscles act in a complex concerted way to bring about the swallowing and vomiting reflexes.

The pharyngeal tube is equipped with sensory nerves which respond to mechanical and chemical stimuli. When food or an object such as a cuffed oropharyngeal airway (e.g., an LMA) is present in the pharynx, swallowing or retching may be provoked depending on the nature, strength, chemical composition, direction, and location of the stimulus. Sensory innervation to the larynx, by contrast, is designed to ensure that nothing injurious gets past the vocal cords into the trachea or wind-pipe. Such reflex responses may be wholly or partly suppressed by local or general anesthesia.

In addition to local reflex response, both the pharynx and the larynx also respond to signals from the brain. The larynx, apart from its protective functions, is an organ of communication. When pain is registered in the brain, reflex laryngeal activity occurs, permitting humans to signal their distress. If pain is experienced while under the influence of anesthesia, due to an inadequate level of anesthesia being provided, these reflex responses still occur, but may be blunted or uncoordinated. For example, laryngeal spasm leading to complete closure of the vocal cords may occur instead of vocalization, if the patient is inadequately anesthetized in the presence of a strong painful stimulus. The pharyngeal constrictor muscles are also involved in this reflex response and it has been discovered that their tone increases in proportion to the level of the stimulus. Such changes in tone begin to occur well before the dangerous condition of laryngeal spasm develops and well before consciousness returns.

Therefore, if these changes in tone can be detected at an early stage, the anesthesiologist has time to remedy the situation (by deepening anesthesia), thus avoiding the onset of laryngeal spasm. The present invention takes advantage of these phenomena and uses the changes in tone of the pharyngeal constrictor muscles as an indicator of anesthetic depth.

One preferred sensor for measuring the tone of the pharyngeal constrictor muscles is the inflated LMA. When an LMA is located in the fully inserted configuration and inflated appropriately, the resulting intra-cuff pressure, or "cuff pressure" (i.e., the pressure inside the inflated cuff) is a function of the tone or tension of the pharyngeal constrictor muscles. This is because these muscles confine the LMA cuff, or define a large proportion of the space in which the inflated cuff resides. Thus, the intra-cuff pressure registered when the cuff is inflated in the confined space of the throat is largely determined by the resistance offered by the muscular walls of the pharynx as they are stretched by the expanding cuff. It can be shown, for example, that a volume of air injected into an LMA cuff sufficient to generate an intra-cuff pressure of 60 cm $H_2O$ when the LMA is in the fully inserted configuration, generates no significant intra-cuff pressure when the LMA is removed from a patient. This indicates that the volume of air in the cuff which generates an intra-cuff pressure of 60 cm $H_2O$ when the cuff is in the patient's throat is less than the volume necessary to stretch the walls of the cuff itself. Accordingly, if the volume of air injected into the cuff is less than the capacity of the cuff itself, the increase in cuff pressure associated with locating the LMA inside a patient is caused by the pharyngeal constrictor muscles resisting expansion of the cuff. However, if additional volume of air is injected into the cuff so that the cuff's elastic walls are stretched, the intra-cuff pressure will now have a further component due to the elastic energy of the cuff walls themselves, thereby reducing the sensitivity of the cuff as a sensor of pharyngeal muscle tone. Provided that the LMA remains in the fully inserted and appropriately inflated configuration (i.e., inflated to an amount that does not stretch the walls of the cuff and yet forces the cuff walls against the pharyngeal constrictor muscles and enables the cuff to form a seal around the glottic opening), the cuff pressure will vary as a function of the tone of, or degree of resistance offered by, the pharyngeal constrictor muscles.

This tone in turn is related to the reflex feedback coming from the brain as well as local reflex feedback from the sensory information coming from the pharyngeal walls. Both sets of feedback loops may be damped down, or extinguished entirely, depending on the level of anesthesia present. During a surgical operation in which an LMA is used as the airway device, if surgical stimulus starts to become too great for the level of anesthesia, the brain-stem begins to send distress signals to the pharynx and larynx which respond with an increase in tone, the pharyngeal component of which can be detected simply by observing corresponding increases in the intra-cuff pressure of the LMA. This change in tone, which can be detected by monitoring changes in cuff pressure, generally precedes conscious perception of pain. The present invention detects, analyzes, and displays detected changes in tone of the pharyngeal constrictor muscles in real time in order to warn the anesthesiologist in a timely fashion of the need to deepen anesthesia.

Another influence on cuff pressure is the fluctuating pressure in the anatomical airways caused by the generation of gas flow within them as the patient breathes or is caused to breathe artificially. Thus, when an LMA is placed in the fully inserted configuration, the cuff pressure varies in a predictable fashion in accordance with the patient's breathing. For example, during IPPV, when the ventilation machine applies pressure to the airway tube of the LMA (to force the patient to inhale), the cuff pressure will rise. Also, when the ventilation machine stops forcing air into the airway tube of the LMA, the cuff pressure will fall. Fluctuations in cuff pressure also occur when the patient is breathing spontaneously. However, when the patient experiences pain or stress, these deviations in cuff pressure become larger than those associated with normal breathing because the size of patient's airway decreases in response to stimuli. The present invention also monitors those pressure fluctuations and generates an alarm when the fluctuations become larger than is considered normal in the adequately anesthetized patient.

Thus the invention is capable of detecting fluctuations in anesthesia depth by two mechanisms:

(1) by sensing changes in the tone of the constrictor muscles of the throat—a DIRECT effect, since these muscles can be said to squeeze or grip the sensor itself (the sensor being preferably a laryngeal mask) and (2) by sensing changes in the resistance of the airways distal to the sensor (i.e., the larynx, trachea and smaller airway tubes branching from it)—an INDIRECT effect, since the pressure fluctuations so produced are caused by changes in the resistance to inspired and expired gas flow secondary to changes in the diameter of these airway passages. This secondary mechanism occurs because part of the sensor (when it is a laryngeal mask) is in contact with the gas mixture being delivered to and from the lungs and is therefore influenced by the fluctuating pressure of this gas mixture. However, changes in airway pressure are amenable to direct measurement by other known methods so that these INDIRECT effects can be distinguished from the DIRECT effects mentioned in (1) above.

A third factor may further influence this fluctuating pressure: as the chest rises and falls with respiration, small fluctuations occur in the anatomical relations around the mask, which is caused to dip slightly in and out of the thoracic cavity, so that its distal part is subjected to intermittent changes in local pressure.

However, the changes described under (2) above cannot be regarded as reliable, since patients vary considerably in the extent to which their airway muscles react to stimuli (the most extreme examples being those with severe asthma); while the third effect described above may vary considerably according to the patient's body shape, in particular according to where the larynx lies in relation to the thoracic cavity. Thus, while the effects listed under (2) may contribute to the utility of the invention, they should be regarded as secondary mechanisms whose interpretation will require a degree of clinical judgement.

One aspect of the present invention includes monitoring cuff pressure and activating an alarm whenever the cuff pressure exceeds an upper or a lower threshold. This alarm is known as a peak alarm. This aspect also includes methods of automatically adjusting the thresholds.

Another aspect of the present invention includes monitoring cuff pressure over a period of time and activating an alarm if the activity of the cuff pressure (or the deviation of cuff pressure from a mean or other value) exceeds a threshold. This alarm is known as a rate alarm. This aspect also includes methods of automatically adjusting the threshold.

Since an LMA is often used for establishing an airway in the patient, it is extremely convenient to also use the LMA as a sensor for monitoring the tone of the pharyngeal constrictor muscles (and thereby the level of anesthesia). However, it will be appreciated that other devices may be used according to the invention for monitoring the tone of the pharyngeal constrictor muscles (and thereby the level of anesthesia). For example, an endotracheal tube may be modified to include a second cuff for monitoring this tone. Endotracheal tubes generally include a cuff or balloon located at their distal end for forming a seal with the inner walls of the trachea. Endotracheal tubes may be modified according to the invention to include a pharyngeal cuff (i.e., a cuff spaced apart from the cuff located at the tube's distal end) so that the pharyngeal cuff resides in the pharynx when the distal end of the tube is positioned beyond the vocal cords in the trachea. Hence, the tone of the pharyngeal constrictor muscles may be measured (and the patient's level of anesthesia may thereby be estimated) by monitoring the pressure in such an endotracheal tube's pharyngeal cuff. As another example, instead of an LMA, another form of cuffed supraglottic airway device may be used to both (1) ventilate the patient and (2) monitor the tone of the patient's pharyngeal constrictor muscles. In general, any device that includes an inflatable cuff or balloon located in the pharynx or hypopharynx may be used according to the invention to measure the tone of the pharyngeal constrictor muscles and thereby to estimate the patient's level of anesthesia.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE FIGURES

For a fuller understanding of the nature and objects of the present invention, reference should be made to the following detailed description taken in connection with the accompanying drawings in which the same reference numerals are used to indicate the same or similar parts wherein:

FIGS. 6A, 6B, 6C, and 7 also show graphs that illustrate calculations that may be performed for determining whether to activate a rate alarm.

DETAILED DESCRIPTION OF THE PREFERRED EMBODIMENTS

Figure 3A:
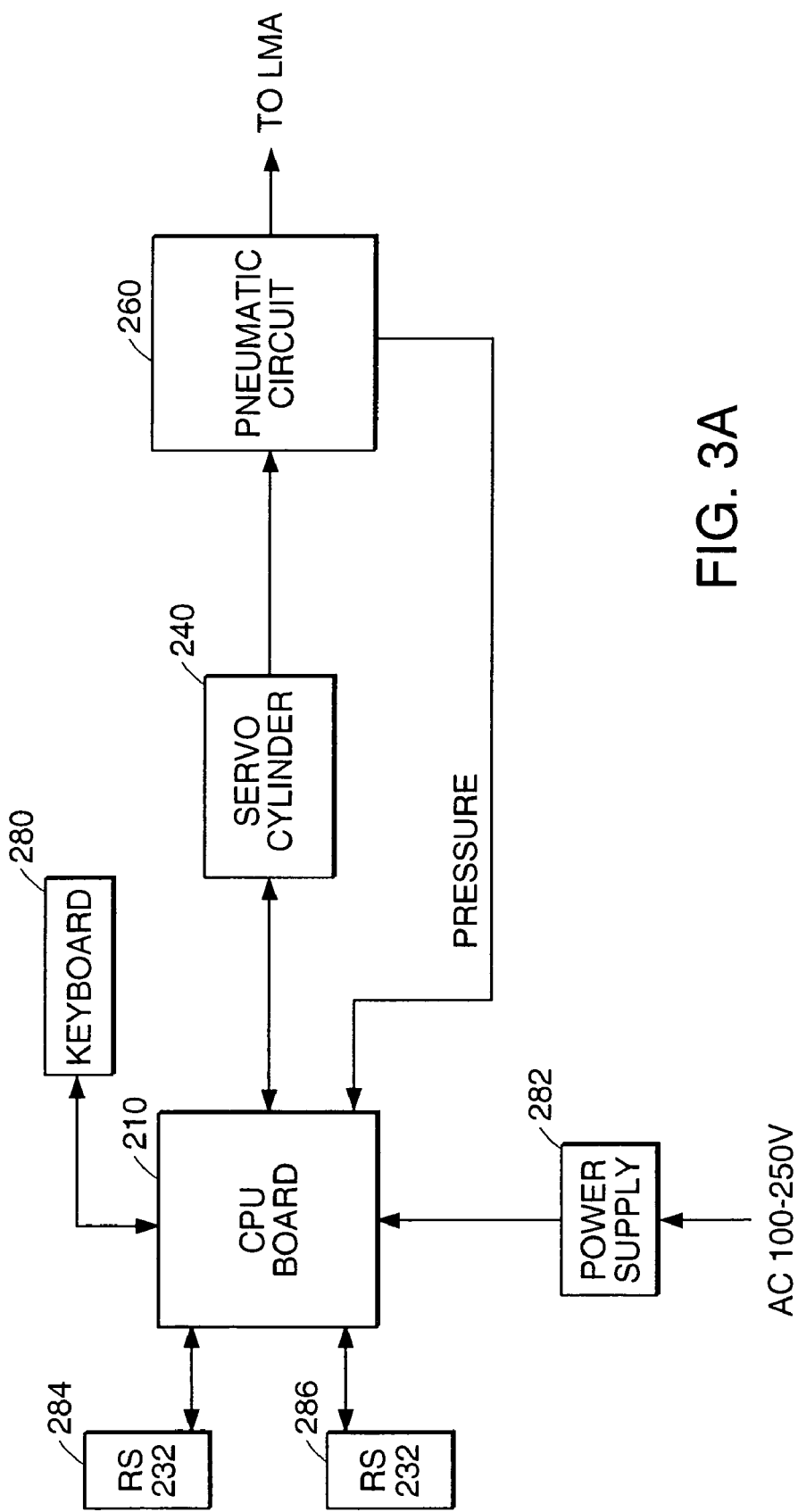
FIG. 3A shows a block diagram of an apparatus constructed according to the invention.

FIG. 3A shows a high level block diagram of an apparatus 200 constructed in accordance with the invention. As discussed above, the LMA is a preferred instrument for monitoring the tone of a patient's pharyngeal constrictor muscles, and apparatus 200 will be discussed principally in connection with the LMA. However, it will be appreciated that apparatus 200 may also be used with other cuff or balloon devices located in the pharynx or hypopharynx.

Apparatus 200 may be used in accordance with the invention for (1) selectively regulating the cuff pressure of an LMA during a surgical procedure; (2) monitoring the cuff pressure of the LMA; (3) analyzing the cuff pressure of the LMA to estimate the anesthetic state of a patient; and (4) generating one or more alarms when the estimated anesthetic state is insufficient for the surgical procedure being performed. As shown, apparatus 200 includes a central processing unit (CPU) board 210, a servo cylinder 240, a pneumatic circuit 260, a key board 280, and a power supply 282. Keyboard 280 may be used for controlling the apparatus 200. Two RS232 interfaces 284, 286 are also provided for input and output of data to and from the CPU board 210.

Figure 1:
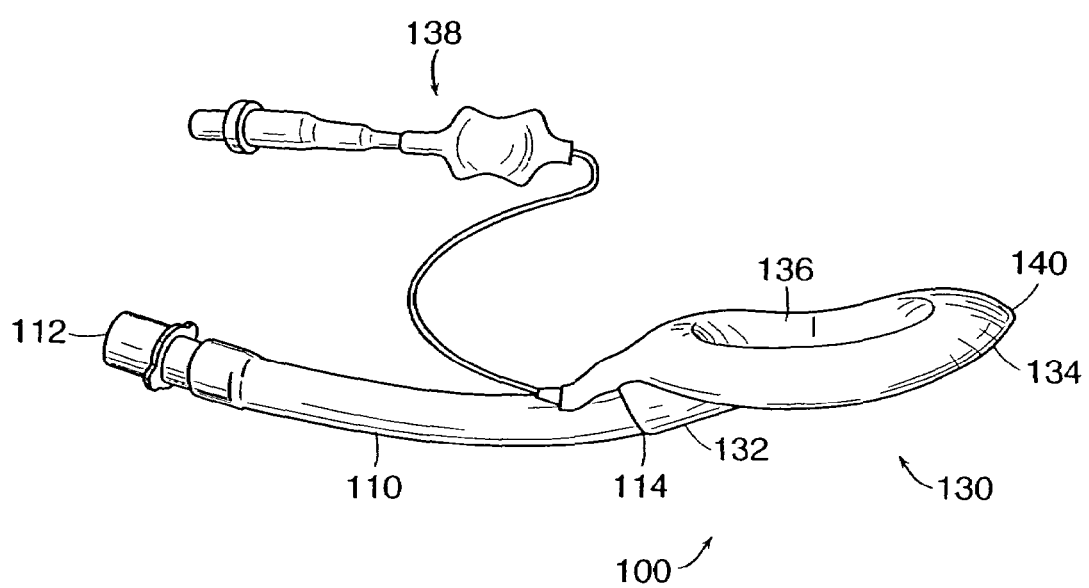
FIG. 1 shows a perspective view of a prior art LMA.
Figure 2:
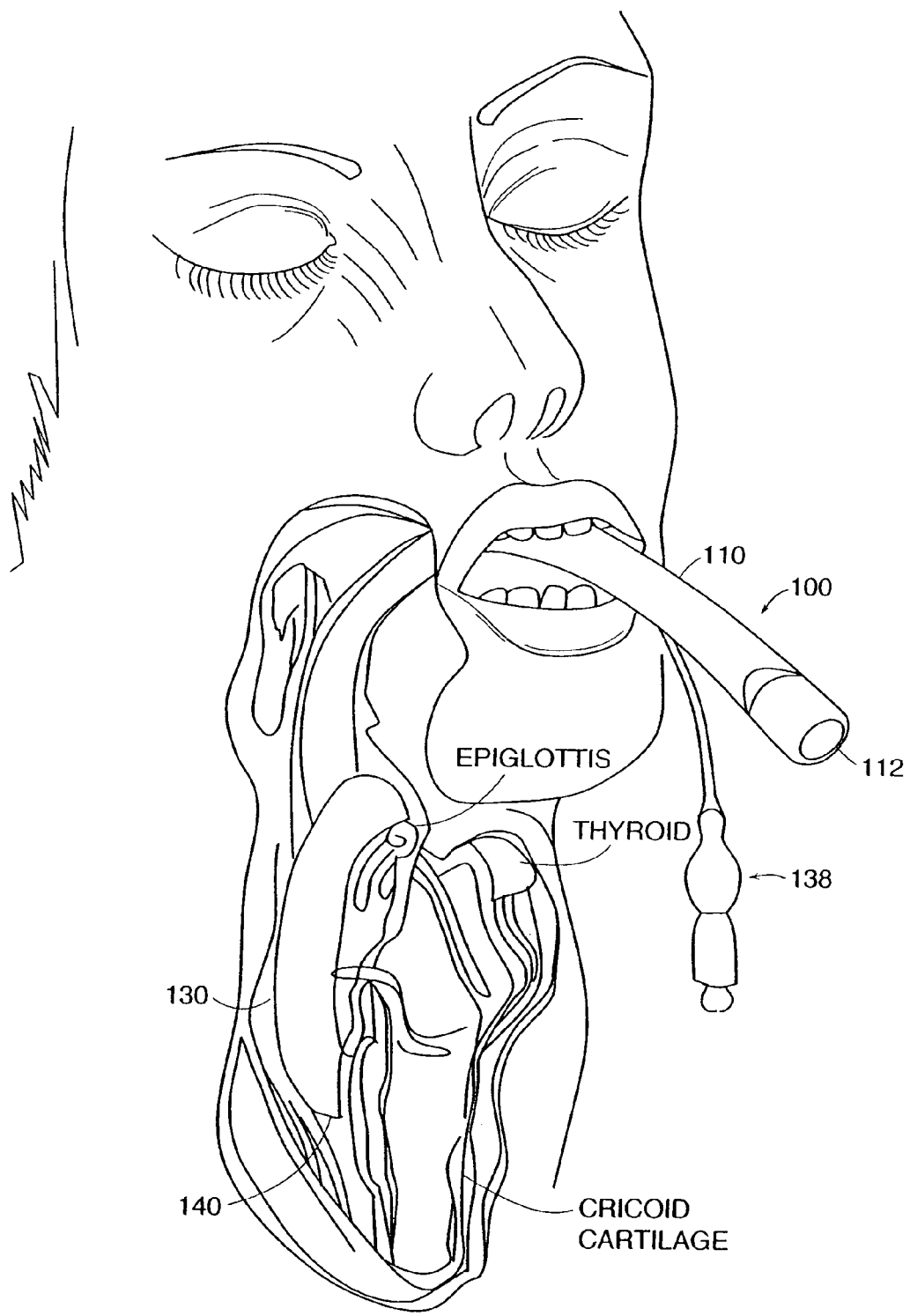
FIG. 2 shows a prior art LMA that has been inserted into a patient.
Figure 3B:
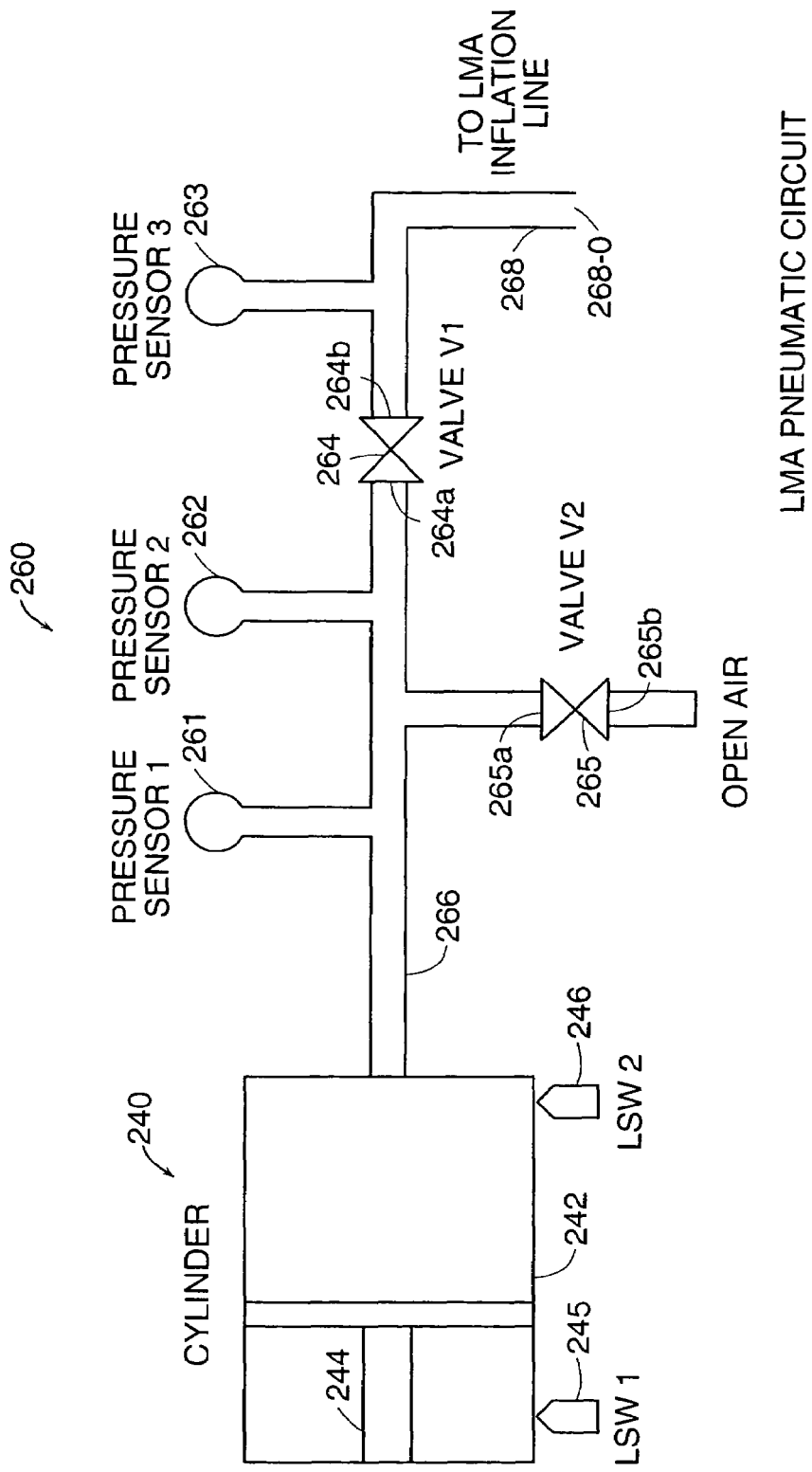
FIG. 3B shows a diagram of the pneumatic circuit of the apparatus shown in FIG. 3A.

FIG. 3B shows a diagram of a the pneumatic circuit 260 and a portion of the servo cylinder 240. As shown, pneumatic circuit 260 includes a first pressure sensor 261, a second pressure sensor 262, a third pressure sensor 263, a first valve 264, a second valve 265, a first pneumatic channel 266, and a second pneumatic channel 268. As is also shown, servo cylinder 240 includes a pneumatic cylinder 242. The following components are all pneumatically coupled together via the first pneumatic channel 266: the first and second pressure sensors 261, 262, one end 264A of valve 264, one end 265A of valve 265, and an output of the pneumatic cylinder 242. The other end 264B of valve 264 and the third pressure sensor 263 are pneumatically coupled to the second pneumatic channel 268. The second pneumatic channel 268 also defines an open end 268-O that may be connected to an inflation line of an LMA (e.g., such as inflation line 238 as shown in FIGS. 1 and 2). Finally, the other end 265B of valve 265 is connected to the open air (or the atmosphere).

When valve 264 is closed, pneumatic channel 266 is isolated from pneumatic channel 268. Conversely, when valve 264 is open, pneumatic channel 266 is connected to pneumatic channel 268. When valve 265 is closed, pneumatic channel 266 is isolated from the atmosphere. Conversely, when valve 265 is open, pneumatic channel 266 is coupled to the atmosphere. As will be discussed below, valve 265 provides a mechanism for selectively introducing gas from the atmosphere into pneumatic channel 266 and to pneumatic cylinder 242 or for expelling gas from pneumatic cylinder 242 and pneumatic channel 266 into the atmosphere. The CPU board 210 controls the operation (i.e., selectively opens and closes) the valves 264 and 265. CPU board 210 also monitors the outputs of the three pressure sensors 261, 262, 263 (and thereby monitors the pressure in pneumatic channels 266 and 268).

Although not shown in FIG. 3B, in addition to pneumatic cylinder 242, the servo cylinder 240 also includes a motor for driving the pneumatic cylinder 242 to either pump air into, or out of, pneumatic channel 266. CPU board 210 selectively drives the motor of servo cylinder 240 for either pumping air into or out of pneumatic channel 266.

In normal operation, when apparatus 200 is initially powered up, and when the open end 268-O of pneumatic channel 268 is initially connected to an inflation line of an LMA, the CPU board 210 will actuate the servo cylinder 240 and the pneumatic circuit 260 so as to pump air into or out of the cuff of the LMA until the cuff pressure reaches a desired value, or "set point". In preferred embodiments, the value of the set point is entered into the CPU board via the communication interfaces 284 or 286; however, a value of the set point may be chosen in other ways (e.g., it may be entered via key board 280). A commonly preferred value for the set point is 60 $cmH_2O$ (in general the set point is preferably selected so that the amount of air introduced into the cuff does not cause stretching of the cuff walls and so that the inflated cuff forms a seal with the glottic opening). In most situations, the cuff pressure will be near the set point when the inflation line is initially connected to apparatus 200 because anesthesiologists generally prefer placing the cuff in the fully inserted configuration before connecting the LMA's inflation line to apparatus 200 (i.e., via end 268-O of channel 268). However, apparatus 200 may also be used to provide the initial inflation of the cuff.

The CPU board may move air into the cuff of the LMA (thereby increasing the cuff pressure) by (1) closing valve 265; (2) opening valve 264; and (3) actuating the servo cylinder 240 so as to move air from the pneumatic cylinder 242 into the pneumatic channel 266. Similarly, the CPU board may move air out of the cuff (thereby decreasing cuff pressure) by (1) closing valve 265; (2) opening valve 264; and (3) actuating the servo cylinder 240 so as to move air from pneumatic channel 266 into the pneumatic cylinder 242. CPU board 210 preferably insures that the pressure in channels 266 and 268 are equal before opening value 264 (e.g., to prevent sudden loss of cuff pressure upon opening of valve 264).

The CPU board may introduce air from the atmosphere into the pneumatic cylinder without affecting cuff pressure by (1) closing valve 264; (2) opening valve 265; and (3) actuating the servo cylinder 240 so as to move air from pneumatic channel 266 into pneumatic cylinder 242. Finally, the CPU board may also vent air from pneumatic cylinder 242 into the atmosphere without affecting cuff pressure by (1) closing valve 264; (2) opening valve 265; and (3) actuating the servo cylinder 240 so as to move air from pneumatic cylinder 242 into pneumatic channel 266.

In one embodiment, the pneumatic cylinder includes a piston 244. As shown in FIG. 3B, moving the piston 244 to the right moves air from the cylinder 242 into channel 266. Conversely, moving the piston 244 to the left moves air from the channel 266 into the cylinder 242. In this embodiment, the servo cylinder 240 also includes two limit switches 245, 246. Switch 245 detects when piston 244 is in its extreme left position and switch 246 detects when piston 244 is in its extreme right position. In operation, if CPU board 210 is reducing cuff pressure and detects that piston 244 is at or near the extreme left position, CPU board 210 preferably closes valve 264, opens valve 265, and actuates the servo cylinder so as to move piston 244 to a central position thereby venting air from cylinder 242 without affecting cuff pressure. Thereafter, CPU board 210 may close valve 265, equalize the pressures in channels 266 and 268 (e.g., by moving air from cylinder 242 into channel 266), open valve 264, and continue withdrawing air from the cuff. Similarly, if CPU board 210 is increasing cuff pressure and detects that piston 244 is in the extreme right position, CPU board 210 preferably closes valve 264, opens valve 265, and moves the piston 244 to a central position thereby moving air from the atmosphere into cylinder 242 without affecting cuff pressure. Thereafter, CPU board 210 may close valve 265, equalize the pressures in channels 266 and 268, open valve 264, and continue moving air into the cuff.

Once the apparatus 200 has brought the cuff pressure to the set point, the apparatus 200 may provide a regulating function of maintaining the cuff pressure at the set point. The regulation function of apparatus 200 will be discussed in greater detail below. In addition to this regulating function, apparatus 200 may also provide a monitoring function, or estimating function, in which the apparatus 200 uses measurements of cuff pressure to estimate the patient's level of anesthesia. Also, as will be discussed in greater detail below, apparatus 200 may perform this estimating function independently of the regulating function (e.g., apparatus 200 may perform its estimating function without also maintaining cuff pressure at the set point). Similarly, apparatus 200 may perform its regulating function without simultaneously performing its estimating function (e.g., apparatus 200 may maintain cuff pressure at the set point without simultaneously estimating the patient's depth of anesthesia).

Figure 4B:
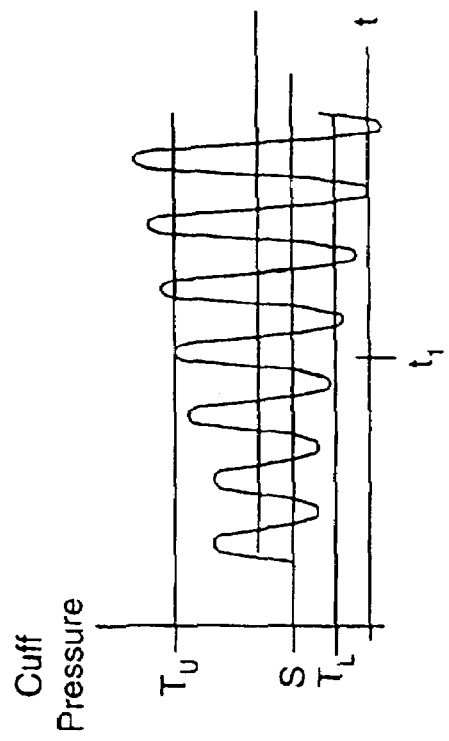
FIG. 4B shows a idealized graph of cuff pressure versus time for a patient that is receiving IPPV and is subliminally experiencing undue stress or pain.
Figure 4A:
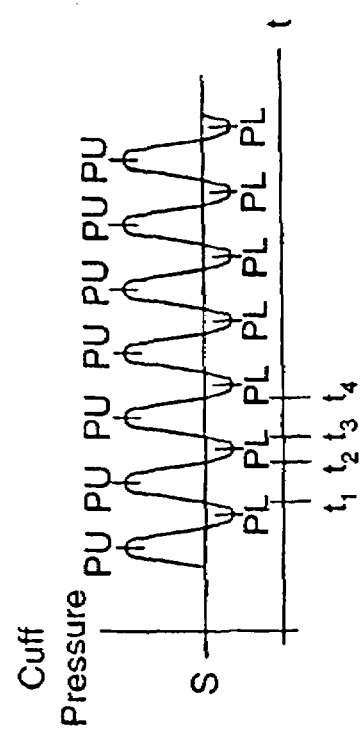
FIG. 4A shows an idealized graph of cuff pressure versus time for a patient receiving IPPV.

The estimating function performed by apparatus 200 will now be discussed. FIG. 4A shows an idealized graph of cuff pressure of an LMA versus time under the following conditions: (1) the LMA has been positioned in the fully inserted configuration within a patient; (2) apparatus 200 has brought the cuff pressure to the set point S; (3) the patient has been generally anesthetized; and (4) IPPV is being applied to the airway tube of the LMA. (FIG. 4A is also generally representative of cuff pressure changes in an LMA versus time during spontaneous breathing.)

As illustrated in FIG. 4A, IPPV tends to cause the cuff pressure to oscillate around the set point S. In FIG. 4A, positive pressure is being applied from a ventilation machine to the airway tube of the LMA (e.g., the proximal end of tube 110 as shown in FIGS. 1 and 2) from time $t_1$ to time $t_2$ and from time $t_3$ to time $t_4$, and this positive pressure forces the patient to inhale during these periods. The ventilation machine does not apply positive pressure during the interval from time $t_2$ to $t_3$ and thereby allows the patient to exhale during this period. Ventilation machines typically deliver either a set volume of gas or a volume of gas determined by a set peak pressure to the patient during each inhalation cycle. FIG. 4A shows the cuff pressure for a period of time during which the IPPV forces the patient to take about seven breaths. Physicians generally adjust the parameters of IPPV so as to cause adult patients to inhale and exhale about ten to fourteen times per minute. Accordingly, FIG. 4A shows cuff pressure for about half of a minute.

As discussed above, when human beings encounter stress or pain, one natural reaction that occurs is an increase in activity or tone of the pharyngeal constrictor muscles. Since cuff pressure varies according to a function of tone of these muscles, an analysis of cuff pressure changes provides an indication of subliminal pain experience which precedes actual awareness. FIG. 4B shows an idealized graph of cuff pressure versus time for the same conditions as described above for FIG. 4A. However, the cuff pressure shown in FIG. 4B is for a patient that is beginning to react to the surgical stimulus at about time $t_1$. As shown, beginning at about time $t_1$, the cuff pressure begins to deviate increasingly from the set point S. In general, the estimating function of apparatus 200 is performed by analyzing the cuff pressure of the LMA and by generating alarms when the deviations of the cuff pressure become larger than is considered normal.

Apparatus 200 preferably generates two different types of alarms: a "peak alarm" and a "rate alarm". Each alarm is generated in response to a different type of detected condition. The peak alarm will now be discussed. As shown in FIG. 4B, an upper threshold $T_U$ and a lower threshold $T_L$ may be defined. Apparatus 200 preferably activates the peak alarm (e.g., by emitting an audible tone) whenever the cuff pressure becomes larger than the upper threshold $T_U$ or smaller than the lower threshold $T_L$. Activation of the peak alarm indicates that the patient's level of anesthesia may be too shallow, or that the patient is about to regain consciousness. The anesthesiologist may decide to increase the amount of anesthetic drugs being administered to the patient in response to the alarm.

The upper and lower thresholds $T_U$ and $T_L$ may be set in a variety of different ways. One simple way is for the upper and lower thresholds to be constant values that are manually entered into apparatus 200 (e.g., via the one of the communication interfaces 284, 286 or via key board 280). However, one problem with using constant values for the thresholds is that the patient's level of activity tends to change during surgical procedures so that, for example, threshold values suitable for the beginning of a procedure may not be suitable for use during the middle of the procedure. Accordingly, apparatus 200 preferably automatically computes new values for the thresholds based on the measurements of cuff pressure.

In one mode of operation, apparatus 200 not only computes new values for the thresholds but also uses the computed values to update the threshold values. That is, in this mode, apparatus 200 automatically updates the values of the thresholds used for the peak alarm over time based on measurements of cuff pressure. In another mode, apparatus 200 never automatically changes the values of the thresholds but instead displays the computed values. The display of the computed threshold value constitutes a recommendation by apparatus 200 to the anesthesiologist that the threshold levels could or should be changed. The anesthesiologist may of course accept, refuse, or ignore the recommendation. The anesthesiologist may indicate acceptance of the recommendation by for example depressing a button on the key board. When the recommendation is accepted, apparatus 200 replaces the current values of the peak thresholds with the computed values. The anesthesiologist may also of course manually enter new threshold values at any time.

One preferred method of computing new peak threshold values will now be discussed. Apparatus 200 preferably executes a "peak finding" algorithm for identifying upper and lower peak values (or extreme values) of the cuff pressure. In FIG. 4A, all the upper peaks of the cuff pressure curve are labeled as PU and all the lower peaks are labeled as PL. Apparatus 200 preferably computes new threshold values based on the detected peak values. The values of the upper peaks PU and lower peaks PL are preferably referenced to a mean or average value of cuff pressure. So, for example, if the mean value of cuff pressure is 60 cm $H_2O$, and the raw or absolute value of a particular upper peak is 65 cm $H_2O$, the upper peak is said to have a value of 5 cm $H_2O$. Similarly, if the raw value of a particular lower peak is 58 cm $H_2O$, the lower peak is said to have a value of minus 2 cm $H_2O$. In the equations described below, the values of the upper and lower peaks will be assumed to be values that have been referenced to a mean value (as just described) as opposed to raw values.

Equation 1A below shows a preferred method for computing new values of the upper peak threshold $T_U$. Equation 2A shows a similar method for computing new values of the lower peak threshold $T_L$. In Equations 1A and 2A (and 1B and 2B further below), $T_U$new represents the new proposed value of the upper threshold $T_U$, $T_U$old represents the current value of the upper threshold $T_U$, $T_L$new represents the new proposed value of the lower threshold $T_L$, $T_L$old represents the current value of the lower threshold $T_L$, $\overline{PU}$ represents an average (or mean value) of several of the upper peak values, $\overline{PL}$ represents the average value of several of the lower peak values, and $\delta(x)$ represents a function that will be discussed below. Note that in Equations 1A and 2A, the threshold values $T_U$new and $T_L$new are also values that are referenced to a mean value of cuff pressure. For example, a value of $T_U$new equal to seven cm $H_2O$, translates to a raw value of 67 cm $H_2O$ if the mean value of cuff pressure equals 60 cm $H_2O$.

$$T_U\text{new} = ((\overline{PU}) * \delta(\overline{PU})) \quad \text{(Equation 1A)}$$

$$T_L\text{new} = ((\overline{PL}) * \delta(\overline{PL})) \quad \text{(Equation 2A)}$$

One preferred value to use for $\overline{PU}$ (and $\overline{PL}$) is the average of the previous eight upper peak values PU (and the average value of the previous eight lower peak values PL), although it will be appreciated that using eight values is a matter of convenience and other numbers of peaks could be averaged to generate $\overline{PU}$ (and $\overline{PL}$). As discussed above, the new values of the thresholds $T_U$new and $T_L$new are preferably displayed to the anesthesiologist as recommendations for updating the values of the peak thresholds.

It may be advantageous for apparatus 200 to use algorithms for insuring that the detected peak values used according to Equations 1A and 2A are "true peaks" and are not artifacts. One such algorithm is to use the previously detected eight peaks as long as those peaks were detected within a time period that is less than or equal to two minutes. This algorithm tends to insure that the detected peaks are generated as a result of actual breathing cycles as opposed to artifacts. For example, if the algorithm detects eight upper peaks within a thirty second period, then those eight peaks are averaged and used according to Equation 1A to compute the upper threshold value. As another example, if the algorithm detects eight lower peaks in ninety seconds, then those eight peaks are averaged and used according to Equation 2A to compute the lower threshold value. However, if the peak detection algorithm doesn't detect eight adjacent peaks in less than two minutes (e.g. only six peaks are detected within two minutes), then all those peaks are discarded and the peak detection algorithm is restarted to look for peaks in the current data.

It will be appreciated that the upper and lower thresholds $T_U$ and $T_L$ are calculated with reference to a mean value of cuff pressure (e.g., an upper threshold value of 5 cm $H_2O$ translates to a raw value of 65 cm $H_2O$ if the mean value of cuff pressure equals 60 cm $H_2O$). One value that may be used for the mean value is the mean value of the cuff pressure during the time interval in which the eight adjacent peaks used to compute the threshold are located. Other methods of calculating or estimating the mean value of cuff pressure may be used as well.

Another useful algorithm for insuring that the detected upper peak values are true peaks is to not count any data point as a peak unless it is greater than 0.1 $cmH_2O$. Yet another algorithm for insuring that detected upper peak values are true peaks is to only count a data point as a peak value if it is the maximal value between two zero crossings (or the maximal value between two points in time where the cuff pressure was less than the mean value). Similar algorithms may of course be used for lower peaks. It will be appreciated that other algorithms may be used for insuring that peaks used to update the thresholds are true peaks and are not artifacts.

New computed values for the upper and lower thresholds $T_U$ and $T_L$ are preferably displayed on a relatively slow time scale (e.g., about once every one or two minutes). One way to provide updates on this relatively slow time scale is to use each peak only once in the calculation of a new threshold. In other words, a set of eight peaks are used to compute the threshold and then the threshold is not computed again until eight new peaks are detected.

When apparatus 200 is operating in a mode in which it automatically updates the threshold it may be advantageous to limit the manner in which apparatus 200 can update the threshold. For example, it is preferred to allow apparatus 200 to update the thresholds so as to make the peak alarm more sensitive (i.e., more likely to be activated) and to not allow apparatus 200 to update the thresholds so as to make the peak alarm less sensitive. One way to accomplish this is have apparatus 200 update the thresholds according to Equations 1B and 2B below.

$$T_U new = \begin{cases} [(\overline{PU}) * \delta(\overline{PU}))] & \text{if } [((\overline{PU}) * \delta(\overline{PU}))] \leq T_U old \\ T_U old & \text{otherwise} \end{cases} \quad \text{(Equation 1B)}$$

$$T_L new = \begin{cases} [((\overline{PL}) * \delta(\overline{PL}))] & \text{if } [((\overline{PL}) * \delta(\overline{PL}))] \geq T_L old \\ T_L old & \text{otherwise} \end{cases} \quad \text{(Equation 2B)}$$

Equation 1B will allow the new upper threshold to be less than or equal to the old value of the upper threshold, but will never let the new upper threshold become greater than the old value of the upper threshold. Similarly, Equation 2B will allow the new lower threshold to be greater than or equal to the old value of the lower threshold, but will never let the new value of the lower threshold to become less than the old value of the lower threshold. In other words, Equations 1B and 2B allow apparatus 200 to become more sensitive (i.e., increase the likelihood that a peak alarm will be set) and will not allow apparatus 200 to become less sensitive. When operating in this mode, apparatus 200 may still display the threshold values computed according to Equations 1A and 2A as recommendations, regardless of whether the new values will make the alarm more or less sensitive. However, in this mode apparatus 200 will only automatically adjust the thresholds if the adjustment makes the alarm more senstive.

At the beginning of a procedure before the patient is fully anesthetized, the variations in cuff pressure tend to be quite large. At this time, the personnel attending the patient are generally fully aware that the patient is not fully anesthetized. Accordingly, at this time there is no need for sounding the peak alarm. To avoid activating the peak alarm, the threshold values may be set to artificially large numbers. However, once the thresholds have been so set, apparatus 200 preferably begins to automatically update the thresholds using Equations 1B and 2B as described above. As the patient's anesthetic state becomes deeper and deeper, apparatus 200 will adjust the threshold values according to Equations 1B and 2B to levels appropriate for the present state of anesthesia. As the patient's anesthetic state becomes lighter (or the patient becomes more conscious), the peak alarm is likely to be frequently or constantly triggered. At this time, if the personnel attending the patient judge that the patient's anesthetic state is appropriate, they may accept the new threshold values recommended by apparatus 200 (computed according to Equations 1A and 2A), which will make the alarm less sensitive, or they may manually adjust the threshold values to levels that will stop the peak alarm from being triggered. Thereafter, apparatus 200 will continue to adjust the threshold values according to Equations 1B and 2B.

Apparatus 200 could of course be operated in a mode in which the apparatus 200 automatically updates the threshold values according to Equations 1A and 2A regardless of whether the update makes the peak alarm more or less sensitive. However, it is generally believed that it is too dangerous to allow a machine, such as apparatus 200, to update the thresholds in a way that makes the alarm less sensitive.

The function $\delta(x)$ referred to above in connection with Equations 1 and 2 will now be described. Equation 3 below shows a preferred method for calculating $\delta(x)$.

$$\delta(x) + (1 + p + \kappa)$$

where (Equation 3)

$$\kappa = \left(\frac{\max - |x|}{\max}\right)$$

$\delta(x)$ may be thought of as being a function of the single variable, x, but there are two parameters that affect the computation of $\delta(x)$, namely, p and max. The parameter p represents a percent value and is preferably a value between zero and one. The value of p may be fixed by apparatus 200 or alternatively may be manually input by the anesthesiologist. Preferred values for p are in the rage of 0.2 to 0.3. The value of max is preferably set by the apparatus 200, and one preferred value for max is 10 $cmH_2O$. Apparatus 200 preferably uses max as a limit on the threshold values. More specifically, apparatus 200 preferably insures that the absolute values of the upper threshold and the lower threshold are never greater than max. Apparatus 200 also uses max in the Equation 3 as shown above. In the preferred embodiment, when calculating $\kappa$, apparatus 200 preferably saturates x at the value of max (i.e., the quantity (max−|x|) is never allowed to be less than zero when computing $\kappa$).

An example of computing a new threshold according to Equation 1 will now be discussed. For this example, the mean value M is 60 $cmH_2O$, the average of the upper peaks $\overline{PU}$ is 5 $cmH_2O$ (i.e., raw value of 65 cm $H_2O$), the value of p is 0.2 (representing twenty percent), the old value of the upper threshold is 10 $cmH_2O$, and the value of max is 10 $cmH_2O$. Using these numbers in Equations 1 and 3 to solve for the new upper threshold yields a result of 7.5 $cmH_2O$. It will be appreciated that increasing the value of the parameter p will increase the separation between the new threshold and the peak values.

The rate alarm will now be discussed. The above-discussed peak alarm is an "instantaneous alarm", meaning that the alarm is activated whenever the instantaneous value, or current value, of the cuff pressure satisfies a condition. In contrast to the peak alarm, the rate alarm is based on cuff pressure data collected over a period of time. Several different methods may be used for controlling the rate alarm, but, in general the rate alarm measures the extent to which the cuff pressure deviates from a mean value over a period of time.

Figure 5A:
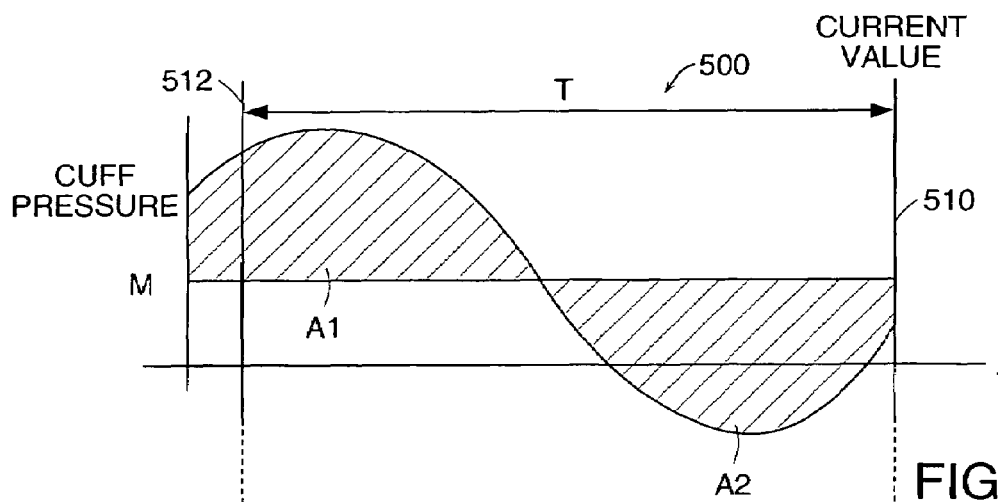
FIGS. 5A and 5B show graphs that illustrate calculations that may be performed for determining whether to activate a rate alarm.

FIG. 5A illustrates one method that may be used by apparatus 200 for controlling the rate alarm. As shown, apparatus 200 defines a time interval (or time window) 500. Interval 500 is characterized by a length T, which may be, for example, twelve and a half seconds. The right end 510 of interval 500 is defined by the current, or present, value of the cuff pressure and the left end 512 of interval 500 is defined by the value of the cuff pressure T seconds prior to the current value. Initially, apparatus 200 calculates the mean value M of the cuff pressure within the interval 500. The calculated mean value M is shown in FIG. 5A. Apparatus 200 then calculates the area A between the cuff pressure curve and the mean value M. In FIG. 5A, the area A is the sum of the shaded area A1 and the shaded area A2. If the area A is greater than a threshold, then apparatus 200 activates the rate alarm (e.g., by emitting an audible tone, preferably a tone that is different than the tone used for the peak alarm). Alternatively, if the area A is less than a threshold, then apparatus 200 does not activate the rate alarm (or deactivates the rate alarm if the rate alarm was previously activated).

Figure 5B:
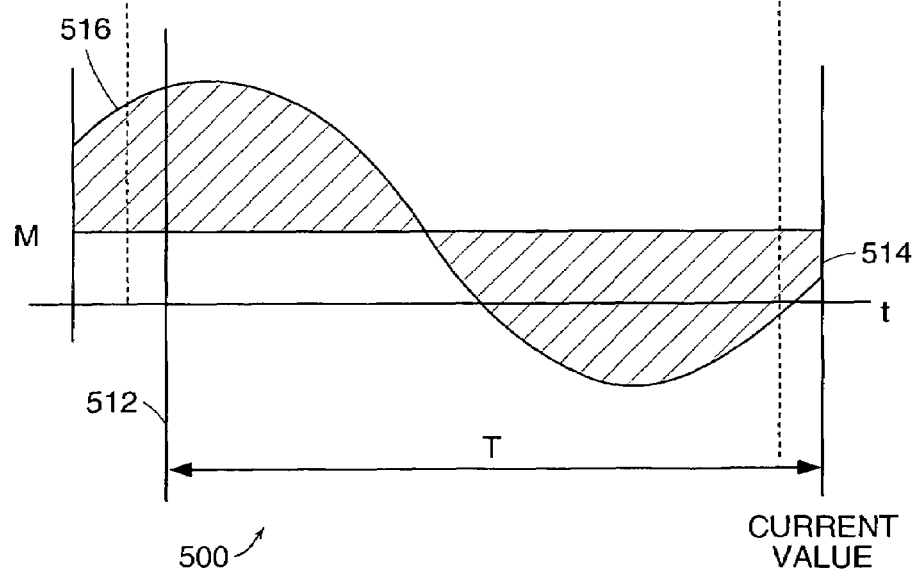

FIG. 5B illustrates the next set of calculations performed by apparatus 200 related to the rate alarm (i.e., the calculations performed after those illustrated in FIG. 5A). As shown in FIG. 5B, the apparatus 200 defines a new interval 500 that is shifted to the right (i.e., shifted forwards in time) from the interval shown in FIG. 5A. Apparatus 200 repeats the calculations for this new interval (i.e., apparatus calculates the mean value of the cuff pressure within the interval and then computes the area between the cuff pressure curve within the interval and the mean value). Once again, if the calculated area is greater than the threshold, then apparatus 200 activates the rate alarm and if the cuff pressure is less than the threshold, then apparatus 200 does not activate the alarm. Apparatus 200 continually advances the interval to the right (i.e., forwards in time) and recalculates the area A to determine whether to activate the alarm.

The calculations discussed above in connection with FIGS. 5A and 5B represent an idealized version of the calculations performed by apparatus 200. However, it will be appreciated that apparatus 200 is a digital system, and in preferred embodiments, CPU board 210 performs a digital approximation of the calculations discussed above in connection with FIGS. 5A and 5B. More specifically, CPU board 210 preferably regularly samples the pressure sensors to measure the cuff pressure. For example, in one embodiment, the CPU board 210 samples the pressure sensors every tenth of a second. The CPU board 210 then defines the time interval 500 so that the right end 510 of the interval intersects the most recent (or current) sample. The interval 500 then includes the most recent sample and all other samples taken T seconds prior to the most current sample. CPU board 210 then calculates the mean value M of all samples of cuff pressure in the interval. Then, to approximate the area between the cuff pressure curve and the mean value M, CPU board 210 preferably calculates the quantity V(n) according to the following Equation 4.

$$V(n) = \sum_{k=n-l}^{k-n} (|p(k) - \text{mean}|) \qquad \text{(Equation 4)}$$

where l is the number of samples in the window

In Equation 4, the "mean" is the average of all the samples of cuff pressure within the interval 500 and the p(k)'s are samples of the cuff pressure within the interval 500. As shown, CPU board 210 calculates the absolute value of the difference between each sample of cuff pressure within the interval 500 and the mean and then sums the absolute values of all the differences. It will be appreciated that this sum of the absolute values of the differences is a digital approximation to the area between the cuff pressure curve and the mean value M.

After calculating the value V(n), CPU board 210 then compares the value V(n) to a threshold. If the value V(n) is greater than the threshold, then CPU board 210 activates the rate alarm. On the other hand, if the value V(n) is less than the threshold, then the CPU board 210 does not activate the rate alarm (and deactivates the rate alarm if the rate alarm had been previously activated). Activating the rate alarm indicates that apparatus 200 has estimated that the patient's level of anesthesia is too shallow, or that the patient is about to regain consciousness. Also, the value of V(n) may be considered as a score that represents the patient's level of anesthesia or level of unconsciousness.

After the value V(n) has been calculated, and the rate alarm has been activated or deactivated appropriately, CPU board 210 then calculates the value V(n+1). As shown in FIG. 5B, the interval 500 used for calculating V(n+1) is generated by shifting the interval used for V(n) to the right by one sample. So, the interval 500 used for V(n+1) includes one new sample 514 that was not included in the interval used for V(n), and the interval 500 used for V(n+1) does not include one old sample 516 that included in the interval used for V(n). With the exception of this one new sample that is included and one old sample that is not included, the samples in the interval used for V(n+1) are identical to the samples in the interval used for V(n), CPU board 210 continually calculates the function V every time a new sample of the cuff pressure is taken and generates the rate alarm based on whether the current value of V is above or below the threshold.

Another method for controlling the rate alarm will now be discussed. According to this preferred method, CPU board 210 computes the quantity V(n) by comparing long term and short term measurements of the mean value of cuff pressure. More specifically, according to this method, CPU board 210 generates the quantity V(n) according to the following Equation 5.

$$V(n) = |M_{lt}(n) - M_{st}(n)| \qquad \text{(Equation 5)}$$

In Equation 5, the quantity $M_{lt}(n)$ represents a "long term" estimation of the mean value of cuff pressure (e.g., the average value of cuff pressure over a fifty second interval) and the quantity $M_{st}(n)$ represents a "short term" estimation of the mean value of cuff pressure (e.g., the average value of cuff pressure over a twelve and a half second interval). The long and short term estimations of the mean $M_{lt}(n)$ and $M_{st}(n)$ are preferably both generated using samples of cuff pressure taken every fifty milliseconds.

FIG. 6A, which shows an idealized graph of cuff pressure versus time, illustrates the calculations performed according to Equation 5. FIG. 6A shows that the long term estimation of the mean value of cuff pressure samples $M_{lt}(n)$ is generated by averaging all samples of cuff pressure taken over the fifty second period $T_1$. FIG. 6A also shows that the short term estimation of the mean value of cuff pressure samples $M_{st}(n)$ is generated by averaging all samples of cuff pressure taken over the twelve and one half second period $T_2$. The value V(n) is then generated according to Equation 5 by calculating the absolute value of the difference between the long and short term estimations of the mean. FIG. 6B illustrates the next calculation of the quantity V(n+1). As illustrated, the next value of V(n+1) is generated by moving the intervals used for computing the long and short term estimations of the mean value of cuff pressure to the right (or forward in time).

Figure 6C:
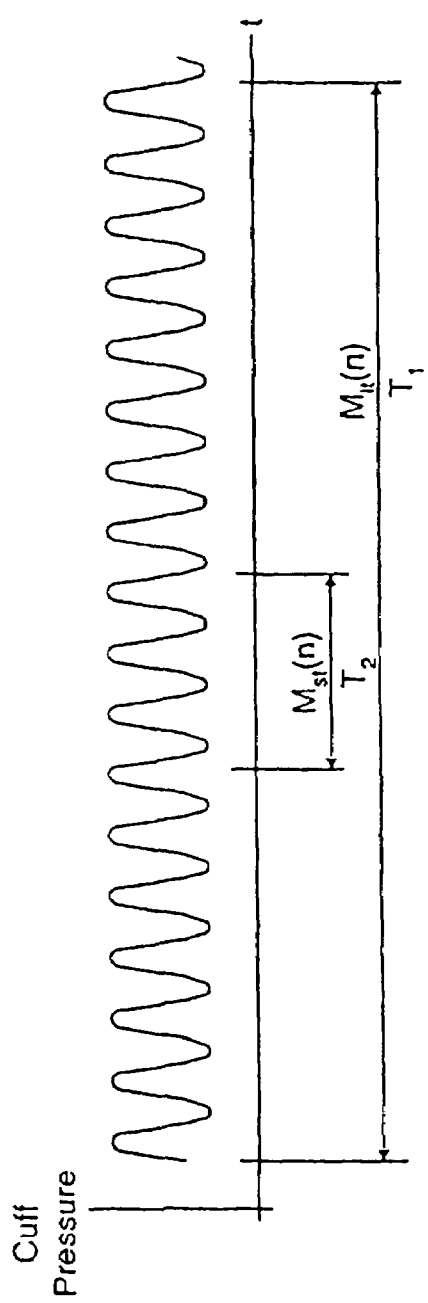

FIG. 6C shows an alternative method that apparatus 200 may use for calculating V(n) according to Equation 5. As shown in FIG. 6C, the long term estimation of the mean $M_{lt}(n)$ is generated by averaging all the samples of cuff pressure taken during the interval $T_1$ and the short term estimation of the mean $M_{st}(n)$ is generated by averaging all the samples of cuff pressure taken during the interval $T_2$. However, in FIG. 6C, the interval $T_2$ occurs in the middle of the interval $T_1$, whereas in FIG. 6A, the interval $T_2$ occurs at the end of the interval $T_1$. It will be appreciated that the relative placement of the intervals shown in FIG. 6A can be advantageous because the value V(n) is updated using the most recently acquired data. However, the relative placement of the intervals shown in FIG. 6C can also be advantageous because the data used for estimating the short term mean $M_{st}(n)$ is surrounded by data used to estimate the long term mean $M_{lt}(n)$.

Figure 7:
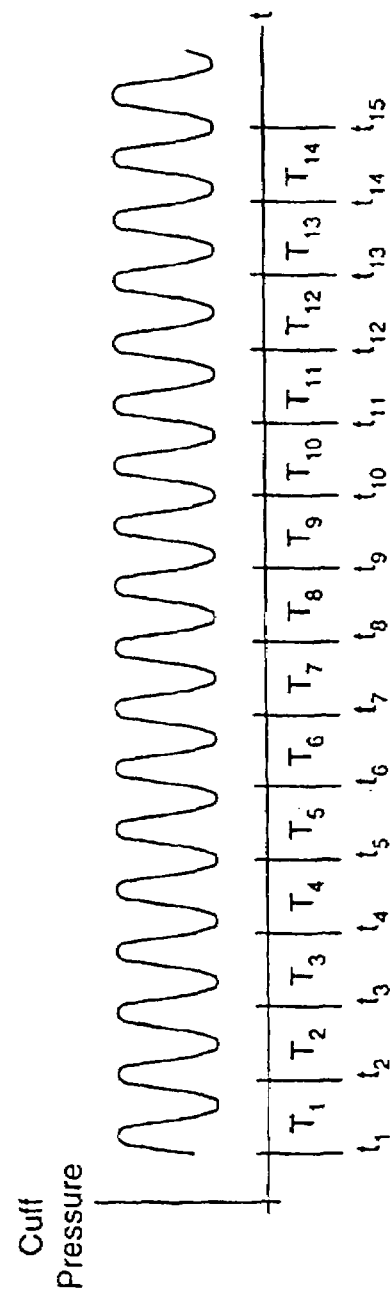

Preferred methods of generating the long and short term estimations of the mean will now be discussed in greater detail. FIG. 7 shows a graph of cuff pressure in which the X-axis (or time axis) has been marked with intervals $T_1$ through $T_{14}$. Apparatus 200 may generate a mean value $MT_X$ for each of the intervals. For example, $MT_1$ is the mean value of all samples taken during interval $T_1$, $MT_2$ is the mean value of all samples taken during interval $T_2$, and so on. Apparatus 200 preferably generates both the long and short term estimations of the mean $M_{lt}(n)$ and $M_{st}(n)$ by averaging groups of the MTs. For example, in one preferred embodiment, the long term estimation of the mean $M_{lt}(n)$ represents an average value of all cuff pressure samples taken within a fifty second interval. One preferred way of generating the long term estimation of the mean is to (1) generate a new MT value every five seconds (i.e., generate an MT value representative of all cuff pressure samples taken within the last five seconds) and (2) average the ten most recently generated MT values. So, for example, if in FIG. 7 each of the intervals $T_1$ through $T_{14}$ is five seconds long, the long term estimation of the mean at time $t_{11}$ would equal the average of all samples of cuff pressure taken between time $t_1$ and $t_{11}$ and could be generated by averaging $MT_1$ through $MT_{10}$. Similarly, the long term estimation of the mean at time $t_{12}$ would equal the average of all samples of cuff pressure taken between time $t_2$ and $t_{12}$ and could be generated by averaging $MT_2$ through $MT_{11}$.

In this same preferred embodiment, the short term estimation of the mean $M_{st}(n)$ represents an average value of all cuff pressure samples taken within a twelve and a half second interval. One preferred way of generating the short term estimation of the mean is to (1) generate a new MT value every one and a quarter seconds (i.e., generate an MT value representative of all cuff pressure samples taken within the last 1.25 seconds) and (2) average the ten most recently generated MT values. So, for example, if in FIG. 6 each of the intervals $T_1$ through $T_{14}$ is 1.25 seconds long, the short term estimation of the mean at time $t_{11}$ would equal the average of all samples of cuff pressure taken between time $t_1$ and $t_{11}$ and could be generated by averaging $MT_1$ through $MT_{10}$. Similarly, the short term estimation of the mean at time $t_{12}$ would equal the average of all samples of cuff pressure taken between time $t_2$ and $t_{12}$ and could be generated by averaging $MT_2$ through $MT_{11}$.

With reference to FIGS. 6A-6C, it will be appreciated that while preferred values for the intervals $T_1$ and $T_2$ are fifty seconds and twelve and one half seconds, respectively, other values could of course be used. Similarly, with reference to FIG. 7, it will be appreciated that the long term and short term estimations of the mean can be calculated in other ways.

As with the method discussed above in connection with Equation 4, when the quantity V(n) is generated according to Equation 5, apparatus 200 activates the rate alarm when the quantity V(n) is greater than a threshold and deactivates the rate alarm when the quantity V(n) is less than a threshold. Although the computations of Equations 4 and 5 are different, they each measure a similar quality, namely, whether the activity of the cuff pressure (or deviation of cuff pressure from a mean) is larger than is considered normal.

As with the upper and lower thresholds discussed above in connection with the peak alarm, the apparatus 200 preferably computes new values of the threshold used for the rate alarm (or the "rate threshold") based on the cuff pressure data. Apparatus 200 may display the new recommended values of the rate threshold without actually updating the rate threshold, or apparatus 200 may actually automatically update the rate threshold. The computation of new recommended values for the rate threshold is preferably performed regardless of how the quantity V(n) is calculated. If apparatus 200 is operating in a mode in which apparatus 200 automatically updates the rate threshold, the automatic adjustments of the rate threshold preferably do not permit the rate alarm to become less sensitive (i.e., they will allow the threshold to grow smaller but will not allow the threshold to grow larger). The preferred method of computing the rate threshold is to simply use the upper peak threshold $T_U$ as the rate threshold (i.e., computed according to Equations 1A or 1B above). In other embodiments, the rate threshold may be generated according to Equation 1 and still be different than the upper peak threshold $T_U$. This may be accomplished by using one set of values of p and max (of Equation 3) for the rate threshold and another set of values for the upper peak threshold. However, preferred values for p and max for the upper peak, lower peak, and rate threshold are all equal (i.e., in the range of 0.2 to 0.3 for peak and 10 $cmH_2O$ for max).

As discussed above, apparatus 200 preferably includes a display for showing the new recommended values of the thresholds. The display of apparatus 200 preferably also shows information related to the alarms. For example, the display preferably shows a graph of cuff pressure versus time. This graph also preferably shows the current values of the upper and lower thresholds that are being used for the peak alarm. The graph accordingly, provides a visual display indicative of when the peak alarm is activated. This graph preferably shows the most recently collected data for some time interval (e.g., the cuff pressure data for the most recent ten or twenty minutes).

Figure 8A:
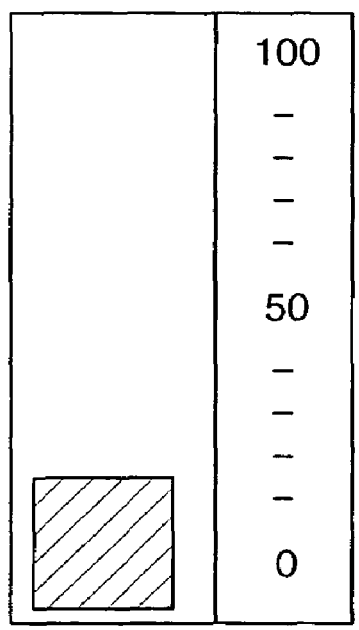
FIGS. 8A and 8B show bar graph displays of patient activity.
Figure 8B:
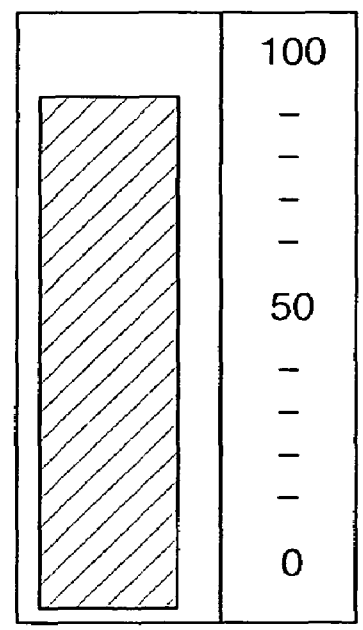

The display may also show information related to the rate alarm. For example, the display may indicate how close the values V(n) are to the rate threshold $T_{rate}(n)$. FIGS. 8A and 8B show one version of this display. As shown, the display comprises a bar graph. The vertical scale on the right extends from zero to one hundred percent. The shaded vertical bar on the right represents the level of a quantity called "patient activity" and is generated according to the following Equation 6. Patient activity can be thought of as a score representative the patient's level of anesthesia or level of unconsciousness.

$$\text{Patient Activity} = 100 * \frac{V(n)}{T_{rate}(n)} \quad \text{(Equation 6)}$$

In FIG. 8A, the shaded bar indicates the patient activity is about twenty percent of the rate threshold. In this case, the rate alarm is not likely to be activated any time soon. In FIG. 8B, the shaded bar indicates that the patient activity is about ninety percent of the rate threshold. In this case, only a slight increase in the value of V(n) will result in activation of the rate alarm.

The bar graphs shown in FIGS. 8A and 8B represent instantaneous comparisons of patient activity to the rate threshold. It may also be advantageous to present a time history of the information presented in the bar graphs shown in FIGS. 8A and 8B. In other words, it may be advantageous to provide a graph that shows the patient activity (as calculated according to Equation 6) for some time interval (e.g., the most recent ten or twenty minutes).

Figure 9A:
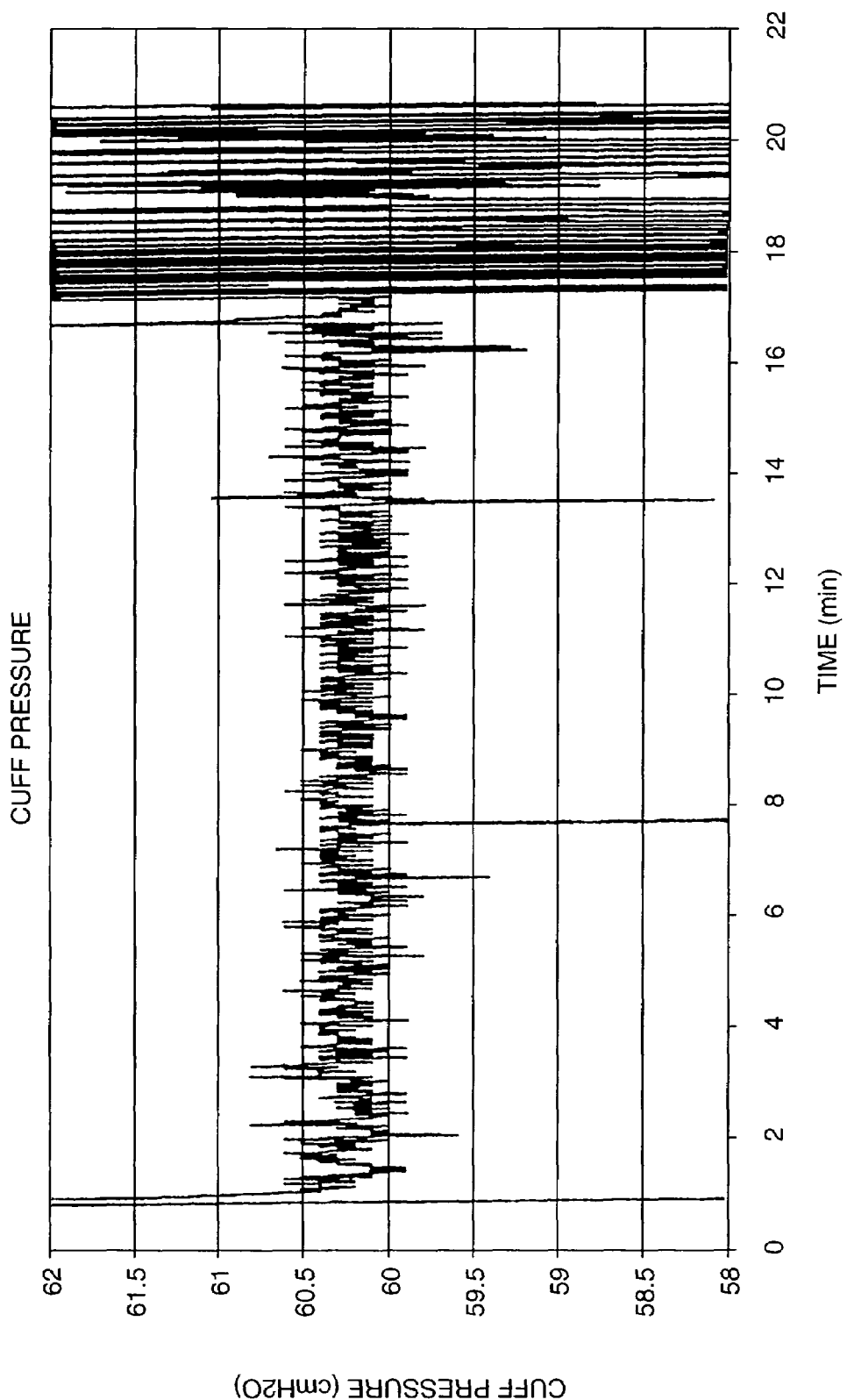
FIGS. 9A and 9B show graphs of cuff pressure taken during a surgical procedure in which an LMA was inserted in the patient.
Figure 9B:
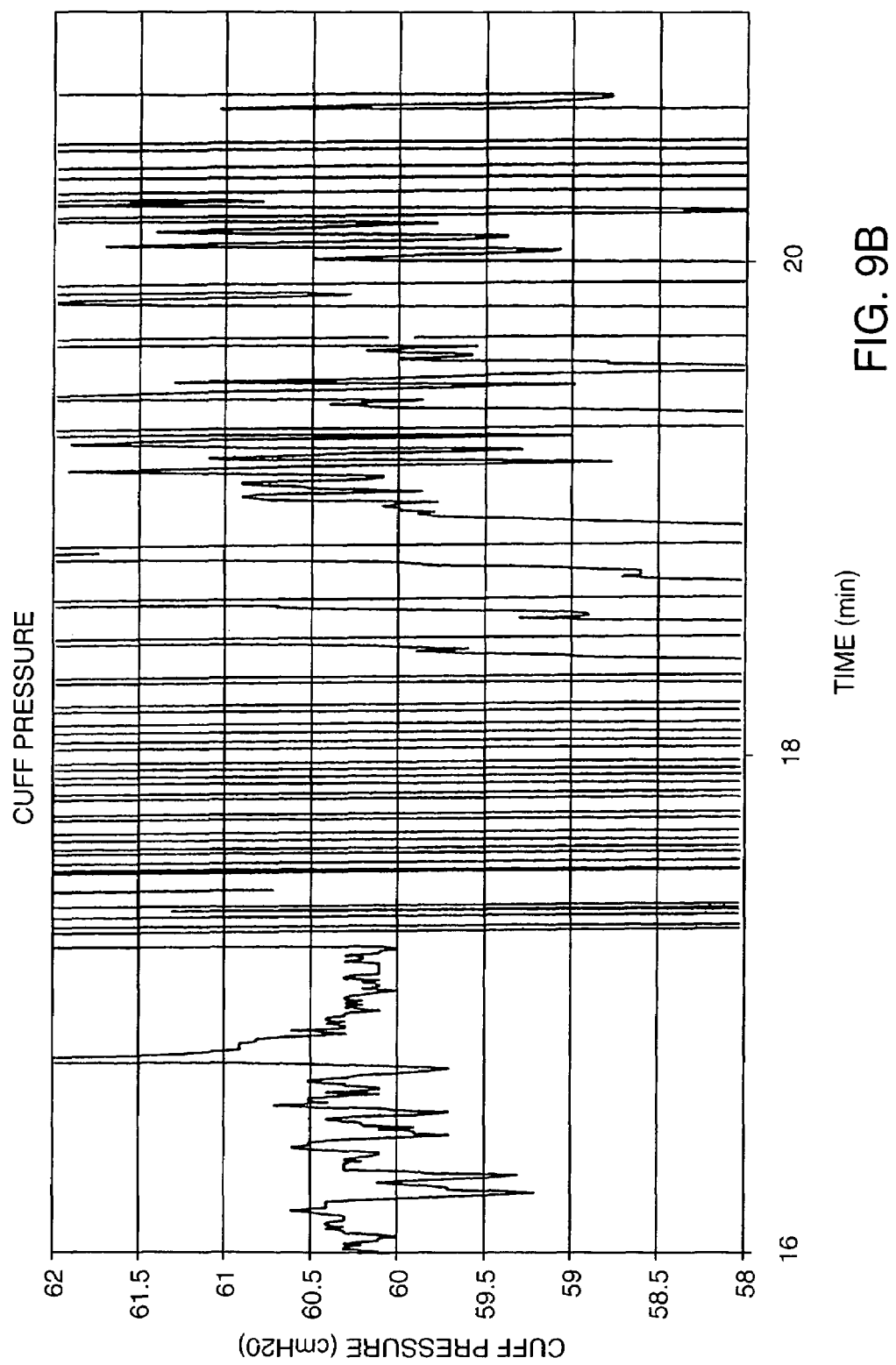

FIGS. 9A and 9B show two graphs of data collected and analyzed by apparatus 200 during an actual surgical procedure. FIG. 9A shows a graph of cuff pressure as measured during the entire twenty-one minute procedure. FIG. 9B shows the same data as FIG. 9A (i.e., cuff pressure measured during the procedure) but has an expanded time scale to show the data from minute sixteen to minute twenty-one. As shown, from about minute two to about minute seventeen, the cuff pressure remained largely within the range of 59.5 to 61 (cmH$_2$O). However, at about minute seventeen, the cuff pressure began to vary over a much larger range. Observation of the patient showed that the patient was beginning to wake up at minute eighteen. The patient also responded to a verbal stimulus at nineteen minutes forty-seven seconds. However, the patient did not exhibit any visible movement before the end of monitoring at twenty-two minutes.

FIGS. 9A and 9B illustrate the basic principles used by apparatus 200. That is, they show that as the patient's level of unconsciousness decreases, the deviations of cuff pressure will increase. It should also be noted that the clearly observable increase in cuff pressure deviations occurred at a time when the patient did not exhibit any observable movement. This also confirms that cuff pressure can be used to detect changes in anesthetic state, or level of consciousness, even in the absence of otherwise observable criteria.

Figure 10A:
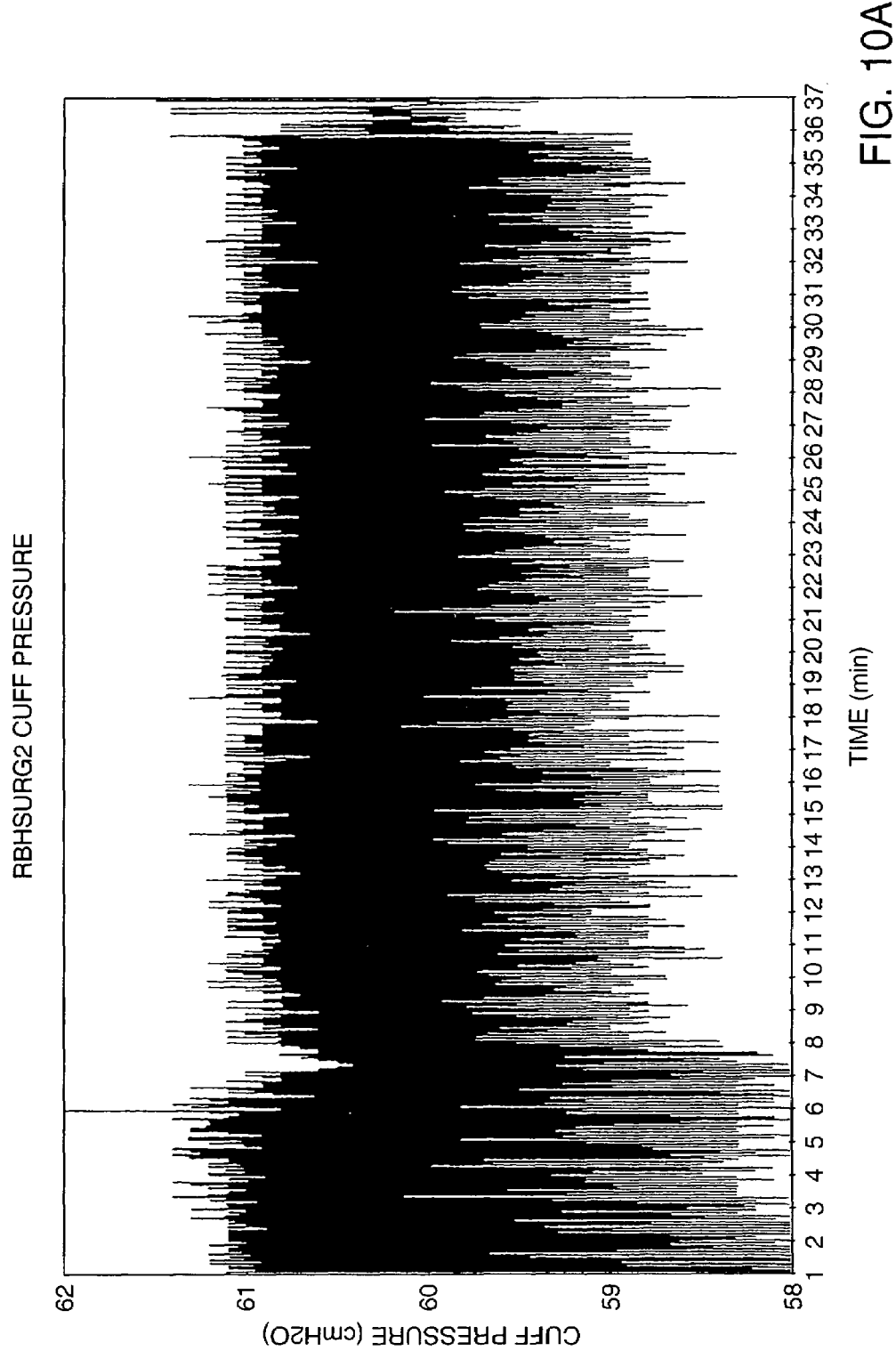
FIGS. 10A and 10B show graphs of cuff pressure taken during a surgical procedure in which an LMA was inserted in the patient.
Figure 10B:
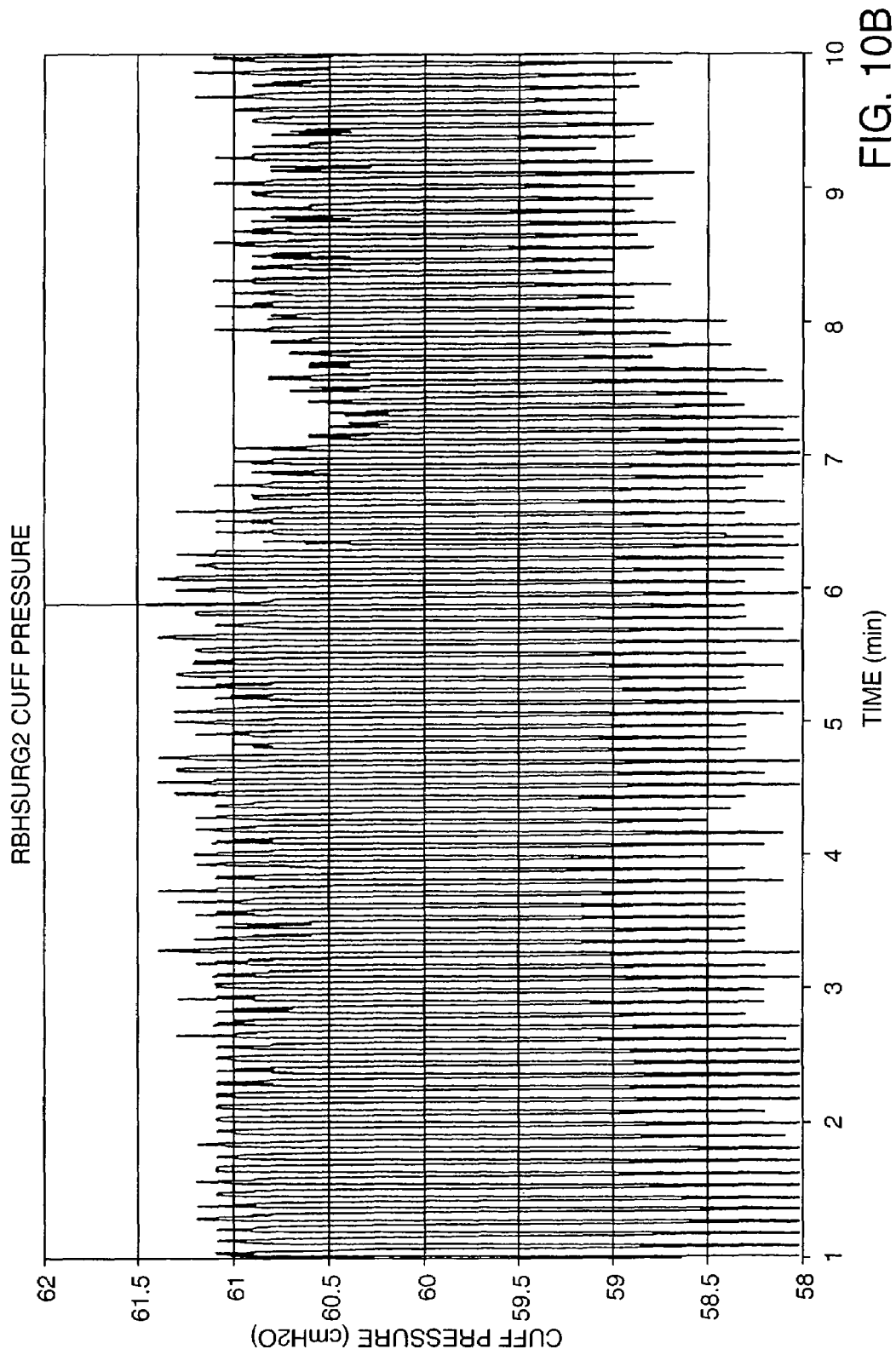
Figure 10C:
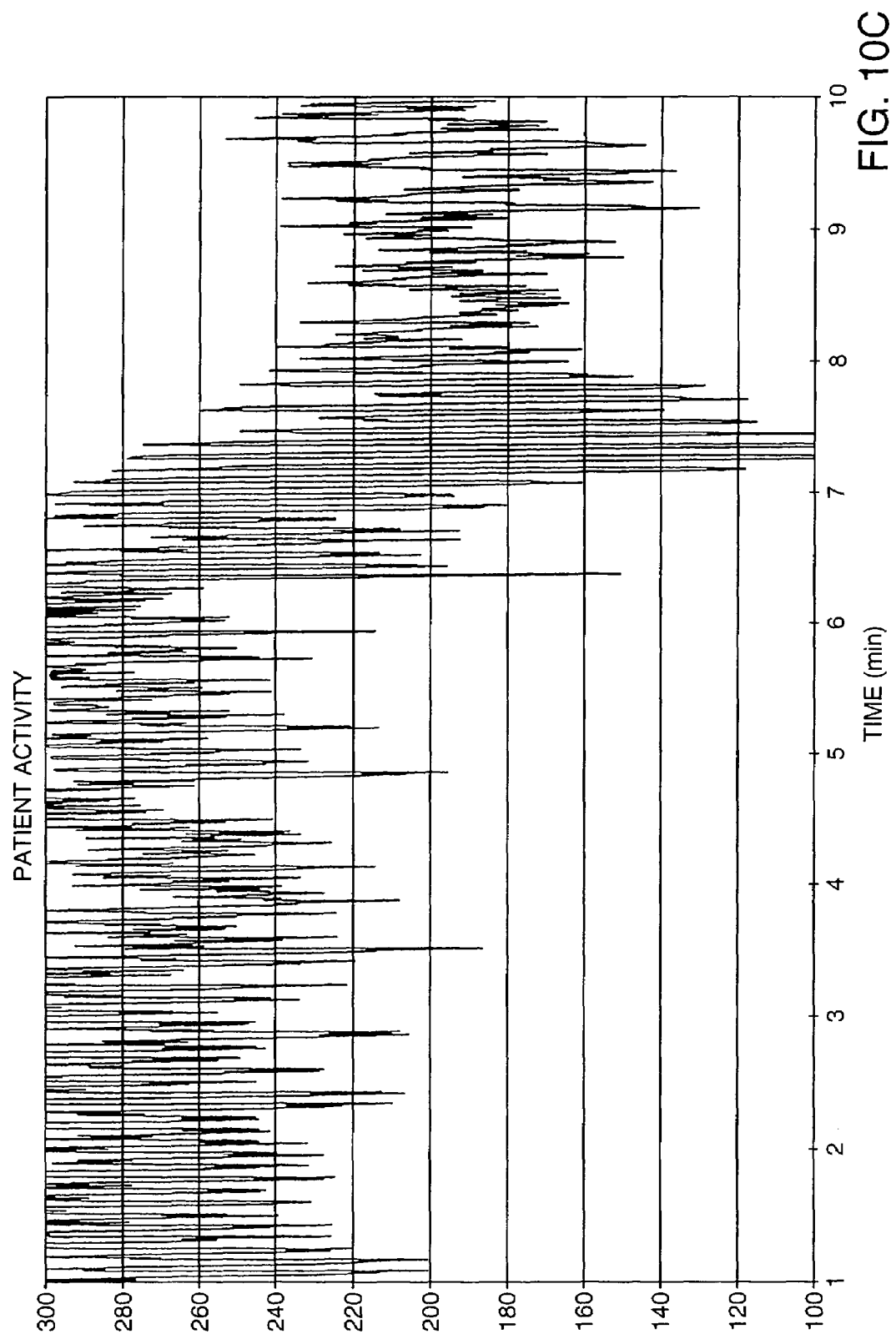
FIG. 10C shows a graph of patient activity during the same procedure associated with FIGS. 10A and 10B.

FIGS. 10A-10C show three graphs of data collected and analyzed by apparatus 200 during another actual surgical procedure. FIG. 10A shows the cuff pressure from the beginning of monitoring to the end of monitoring at minute fifty-six. FIG. 10B shows cuff pressure at an expanded time scale from the beginning of monitoring to minute ten. FIG. 10C shows a graph of the patient activity from the beginning of monitoring to minute ten.

During this procedure, the amount of Propofol (the most common anesthetic agent) delivered to the patient was increased at seven minutes and four seconds to put the patient into a deeper anesthetic state. As shown, the cuff pressure deviations decreased markedly after this increase in the applied Propofol. Consequently, the patient activity, as shown in FIG. 10C, also decreased markedly. These graphs again illustrate the basic principal of the invention. Namely, that as the patient moves into a deeper anesthetic state, the cuff pressure deviations will decrease (and the patient activity will also decrease).

Figure 11A:
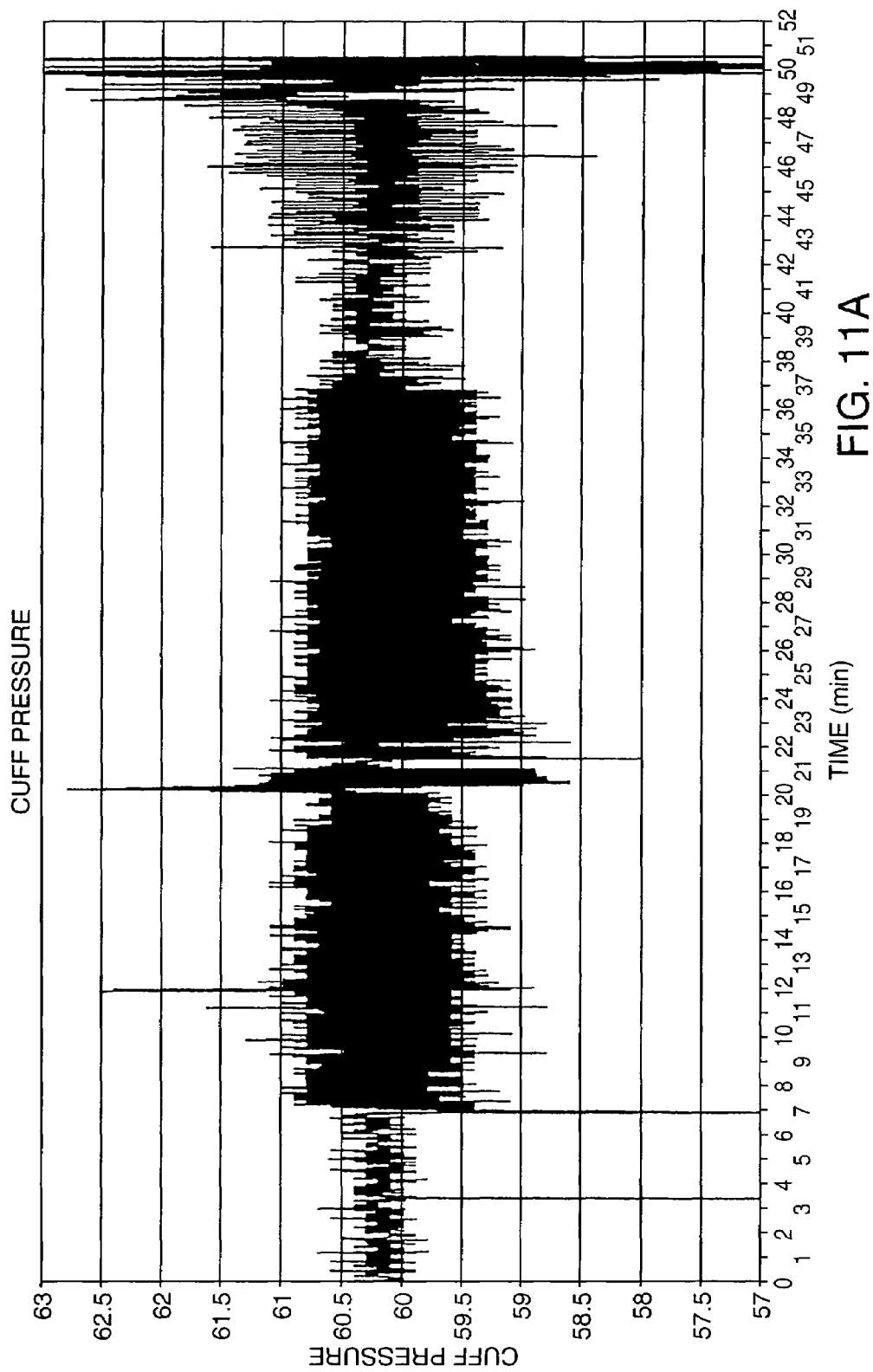
FIGS. 11A, 11B, and 11D show graphs of cuff pressure taken during a surgical procedure in which an LMA was inserted in the patient.
Figure 11B:
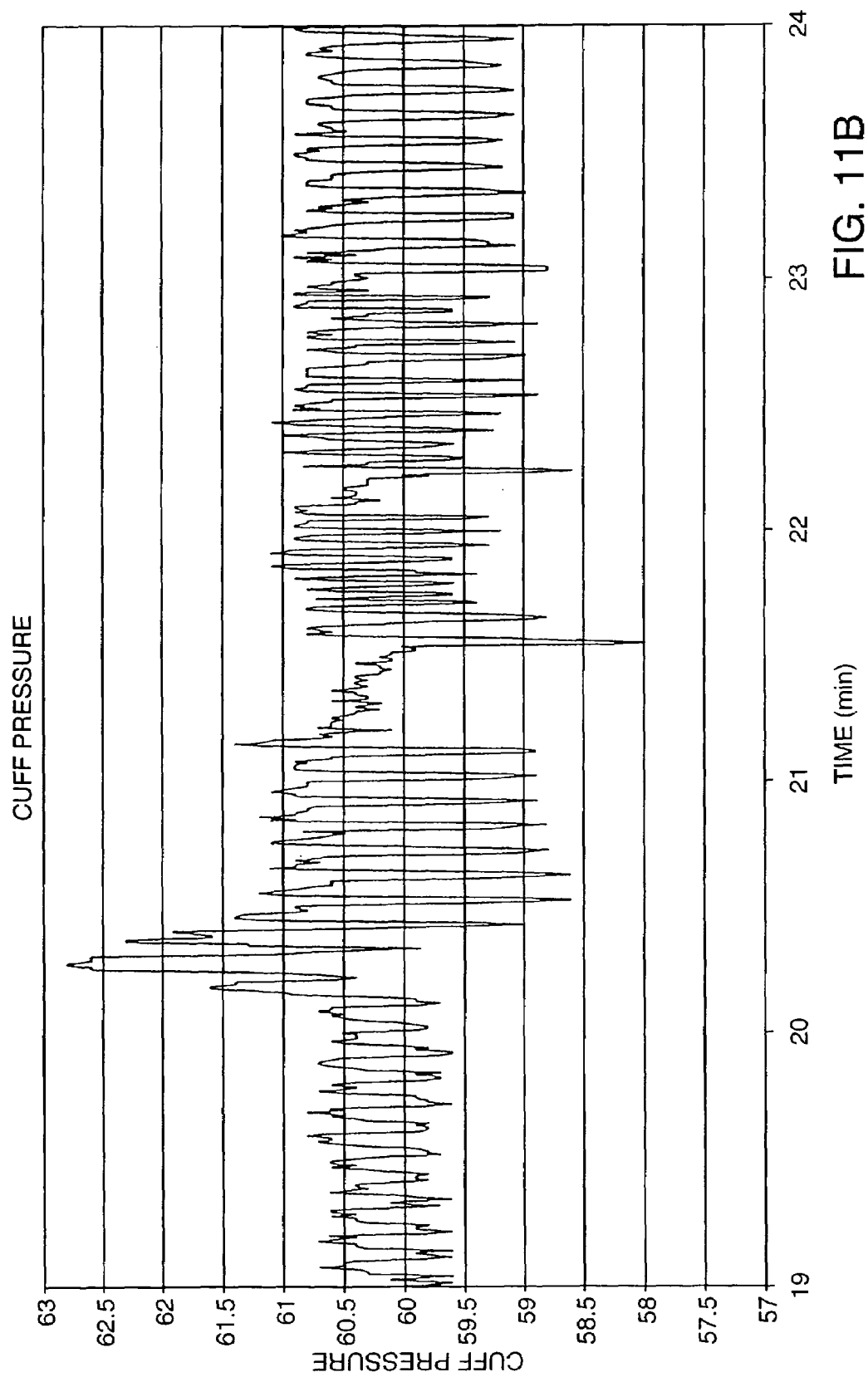
Figure 11C:
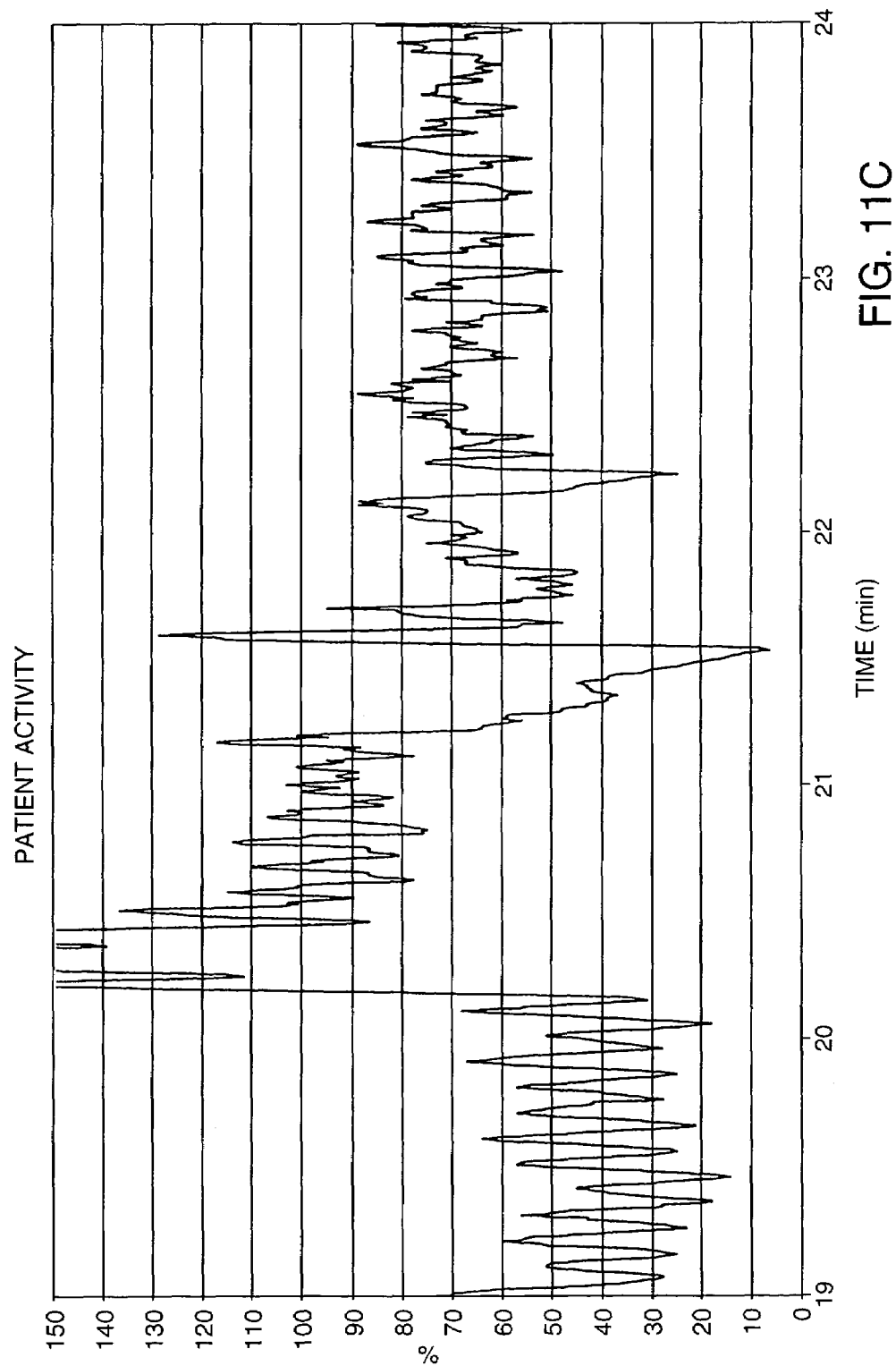
FIG. 11C shows a graph of patient activity during the same procedure associated with FIGS. 11A, 11B, and 11D.
Figure 11D:
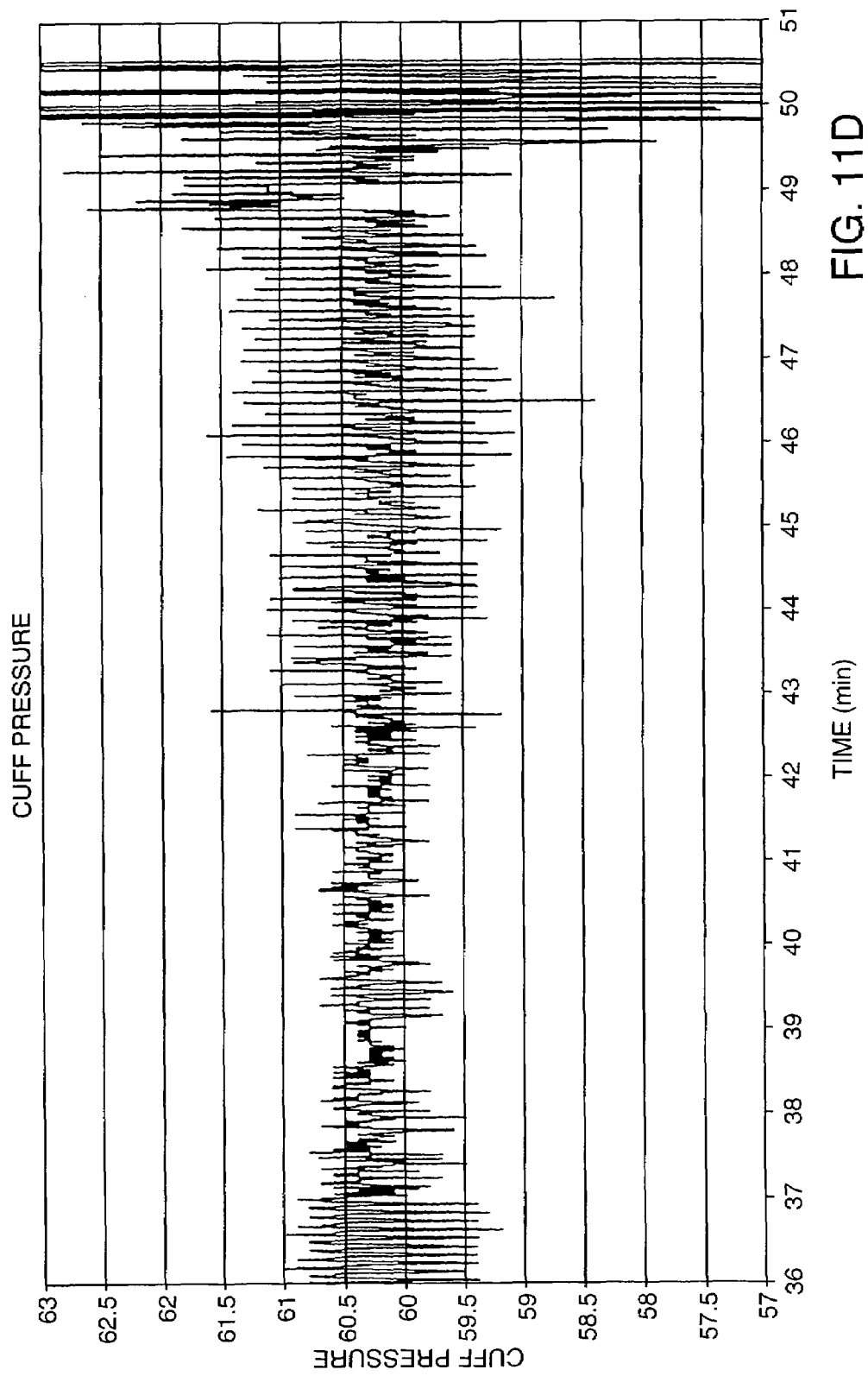

FIGS. 11A-11D show four graphs of data collected and analyzed by apparatus 200 during another actual surgical procedure. FIG. 11A shows cuff pressure from the beginning of monitoring to the end of monitoring at minute fifty-one. FIG. 11B shows cuff pressure on an expanded time scale from minute nineteen to minute twenty-four. FIG. 11C shows a graph of patient activity (as calculated according to Equation 6) from minute nineteen to minute twenty-four. FIG. 11D shows cuff pressure on an expanded time scale from minute thirty-six to the end of monitoring.

During the first seven minutes of this procedure, the inflation line of the LMA was not properly coupled to apparatus 200 and the cuff pressure activity accordingly appeared to be very low. The cuff pressure was relatively stable from minute seven to minute nineteen. The cuff pressure oscillations began to increase at minute twenty and apparatus 200 activated alarms. Additional anesthetic was applied after alarm activation and the cuff pressure oscillations returned to the normal range.

FIG. 11D shows the cuff pressure during the patient's recovery period. IPPV was terminated at minute thirty-seven. The patient received assisted breathing (i.e., bag ventilation) from minute thirty-seven to minute forty-three, and the patient breathed spontaneously thereafter. Increased cuff pressure oscillations at minute 50 was due to swallowing attempts.

FIG. 11D shows patient recovery. IPPV was terminated at minute 37. The patient received breathing assistance until minute 43 via manual bag ventilation. The patient breathed spontaneously from minute 43 onwards. Increased activity at minute 50 was due to the patient attempting to swallow.

Figure 12A:
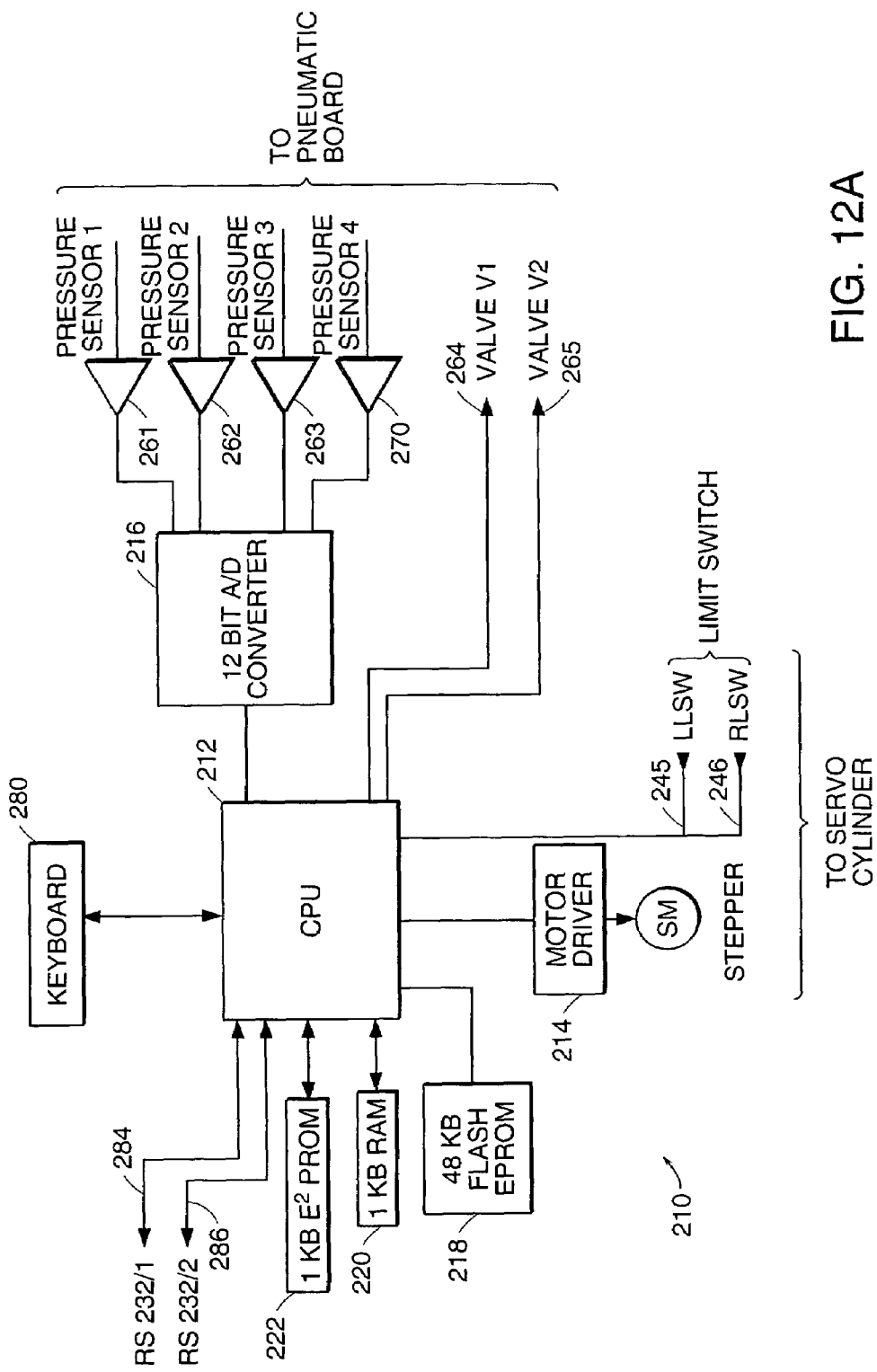
FIG. 12A shows a diagram of the CPU board of the apparatus shown in FIG. 3A.
Figure 12B:
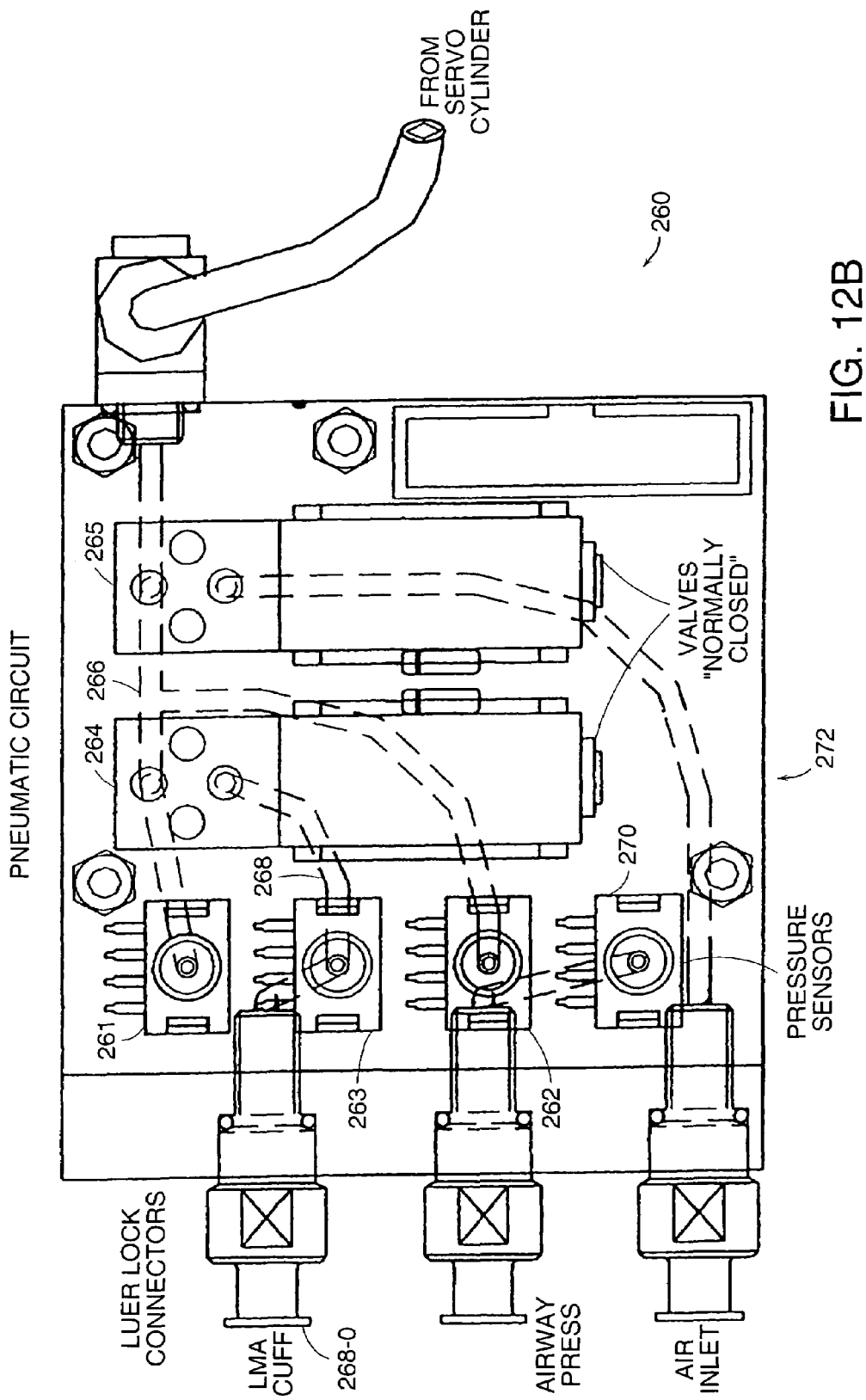
FIG. 12B shows a diagram of a preferred embodiment of the pneumatic circuit shown in FIG. 3B.
Figure 12C:
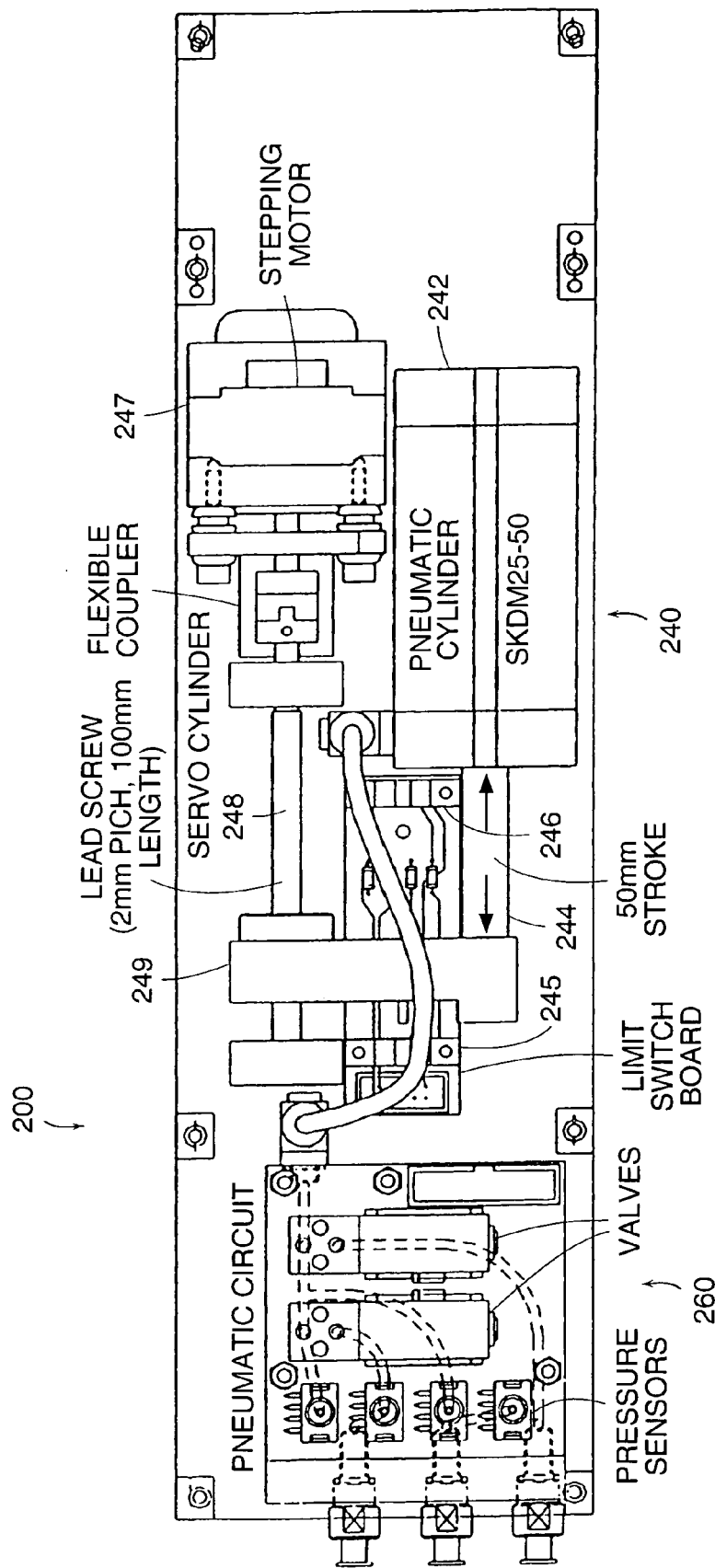
FIG. 12C shows a diagram of the apparatus shown in FIG. 3A showing the connection between the servo cylinder and the pneumatic circuit.

FIGS. 12A, 12B, and 12C show additional details of apparatus 200. More specifically, FIG. 12A shows a block diagram of CPU board 210 (shown also in FIG. 3A). FIG. 12B shows a preferred embodiment of pneumatic circuit 260 (shown also in FIG. 3A). FIG. 12C shows a diagram of several components of apparatus 200.

Referring initially to FIG. 12A, the CPU board 210 includes a microprocessor chip 212, a motor driver chip 214, and an analog-to-digital (A/D) converter chip 216. The analog outputs of the three pressure sensors 261, 262, 263 shown in FIG. 3B are all applied to A/D converter chip 216. In the preferred embodiment, a fourth pressure sensor 270 is also included in apparatus 200 and its analog output is also applied to A/D converter chip 216. This fourth pressure sensor 270 preferably measures the pressure in the airway tube of an LMA (e.g., airway tube 110 as shown in FIG. 1). A/D converter chip 216 periodically converts the analog outputs of each of the four pressure sensors 261, 262, 263, 270 to digital values and applies those digital values to an input of microprocessor chip 212. This permits microprocessor chip 212 to monitor the pressure sensed by each of the four pressure sensors 261, 262, 263, 270. The A/D converter chip 216 may be implemented, for example, using an eight channel, twelve bit analog-to-digital converter. Such devices may be purchased from Analog Devices of Massachusetts (e.g., part number AD7858).

The outputs of key board 280 and limit switches 245, 246 are applied to other inputs of microprocessor chip 212. An output of microprocessor chip 212 is applied to the motor driver chip 214, and the motor driver chip 214 generates signals for driving the motor of servo cylinder 240. In one preferred embodiment, the motor of servo cylinder 240 is implemented using a stepper motor and the motor driver chip 214 may be implemented using a TA8435H which is commercially available from Toshiba of Japan.

Communication interfaces 284, 286 are also coupled to microprocessor chip 212. Some memory is also included on the CPU board 210 for program and data storage. In one embodiment, CPU board 210 includes a 48 kilobyte flash EPROM chip 218, a 1 kilobyte RAM chip 220, and a 1.2 kilobyte electrically erasable PROM chip 222, and memories 218, 220, 222 are coupled to microprocessor chip 212. The microprocessor chip may be implemented for example using an H83334, single chip microprocessor, which is commercially available from Hitachi.

FIG. 12B shows a preferred embodiment of the pneumatic circuit 260. In this embodiment, the four sensors 261, 262, 263, 270 and the two valves 264, 265 are mounted to a solid rectangular block 272. Block 272 provides a convenient material for (1) defining the pneumatic channels 266, 268; (2) coupling the pressure sensors and valves to the pneumatic channels; and (3) preventing leaks. Block 272 preferably includes two equally sized solid rectangular pieces of plexiglass, and block 272 is formed by gluing or bonding the pieces together. More specifically, all solid rectangular shapes define six faces, and block 272 is formed by bonding an inner face of one of the pieces to an inner face of the other piece. Preferably, the inner face of one of the pieces is planar, whereas channels or trenches are cut into the inner face of the other piece to define the pneumatic channels 266, 268. Screws may be used to hold the pieces together, but preferably a bonding agent (e.g., an epoxy) that melts some of the plexiglass is used so as to pneumatically seal the two pieces together.

The valves 264, 265 are preferably normally closed valves (i.e., valves that close in the absence of an actuating signal forcing the valves to open). The valves may be implemented using 24 VDC (volts direct current) valves which are commercially available from Pneutronic by Parker of USA. Such valves are commonly used in medical devices.

The pressure sensors 261, 262, 263, 270 may be implemented using piezoelectric sensors that have an operating range extending from zero to five pounds per square inch. Such sensors are commercially available from Micro Switch of Freeport, Ill. (a division of Honeywell).

FIG. 12C shows a view of apparatus 200 showing the relative positions of the servo cylinder and the pneumatic circuit 260. As shown, servo cylinder 240 includes pneumatic cylinder 242 with piston 244, limit switches 245, 246 which are mounted to a limit switch board, and a stepper motor 247. A lead screw 248 and a coupler 249 are used to transfer motion of motor 247 into motion of piston 244. More specifically, rotation of motor 247 causes rotation of lead screw 248. Threads of lead screw 248 couple with threads of coupler 249 so that rotation of lead screw 248 causes translation (left or right as shown in FIG. 12C) of coupler 249. Coupler 249 is rigidly fixed to piston 244 so translation of coupler causes translation of piston 244 and thereby moves air into or out of cylinder 242.

Pneumatic cylinder 242 may be implemented using a SKDM2550 which is commercially available from Vesta (Rovigo) Italy. This cylinder defines a 25 mm internal diameter bore, a 50 mm stroke (i.e., the range of motion of piston 244 is 50 mm), and a volume of about 20 millilitres. The stepper motor may be implemented using a 103547-5240 which is commercially available from Sanyo-Denky of Japan. This motor operates at 24 V dc, can be driven a 1600 steps per revolution, and delivers a torque of 25 Newton/cm. The servo cylinder is preferably configured so that each full rotation of the stepper motor (i.e., 1600 steps) causes piston 244 to translate by 2 mm (millimeters)

The power supply 282 (shown in FIG. 3A) of apparatus 200 may be implemented using a switching 20 watt 24 volt universal input PSU model 0FM-0205, which is commercially available from by Astrodyne of Taiwan.

The pressure regulation function of apparatus 200 will now be discussed. The general goals of the regulation provided by apparatus 200 are to (1) keep the cuff pressure at a desired value (i.e., the set point) and (2) when the cuff pressure is not at the set point to quickly bring the cuff pressure to the set point without overshooting or oscillating.

Figure 13:
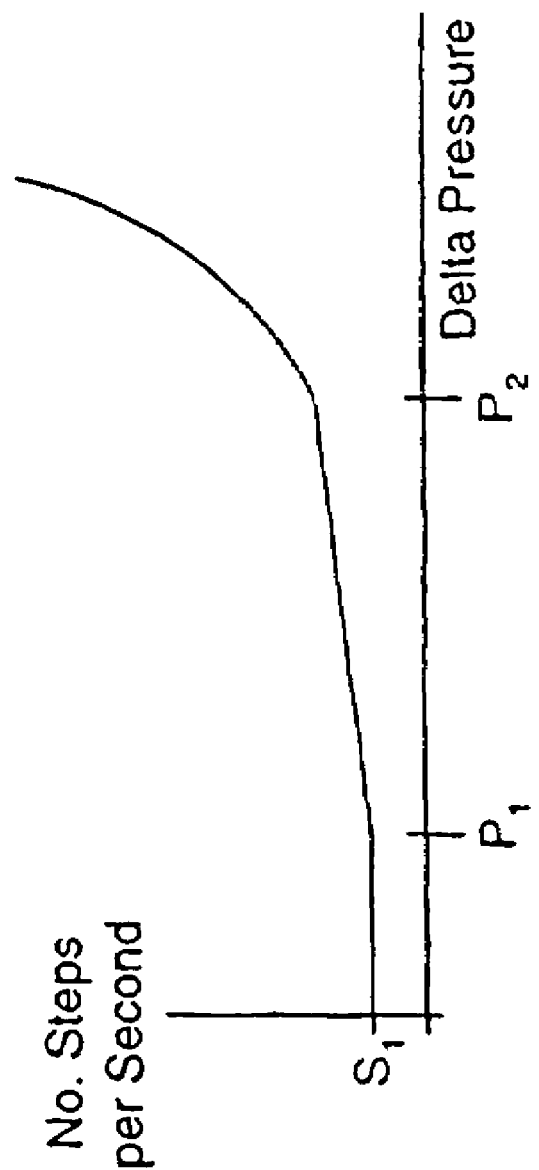
FIG. 13 shows a curve of motor steps versus delta pressure used by the apparatus shown in FIG. 3A for regulating cuff pressure.

FIG. 13 shows a graph that illustrates the basic form of the controller function used by microprocessor 212 for regulating the stepper motor 247 when apparatus 200 is regulating pressure in an LMA cuff. The X-axis of FIG. 13 is labelled "delta pressure" and represents an absolute value of a difference between the set point and the actual pressure of the cuff. In other words, the variable of the X-axis represents the magnitude of the difference between the actual cuff pressure and the desired cuff pressure (i.e., the set point). The Y-axis of FIG. 13 represents the speed (in number of steps per second) of the stepper motor 247. So, FIG. 13 shows the number of steps per second that will be taken by stepper motor 247 for any given delta pressure. In a preferred method of operation, microprocessor chip 212 (1) measures delta pressure once every half a second and (2) every half a second updates the control of stepper motor 247 via driver chip 214 so that the motor rotates at a rate of S steps per second, where S is determined according to the previously measured value of delta pressure and according to the controller curve shown in FIG. 13. So, the microprocessor preferably updates the control of stepper motor 247 once ever half of a second. Also, the microprocessor 212 preferably only causes the motor 247 to move if the measured delta pressure is greater than 0.1 cmH$_2$O.

The curve shown in FIG. 13 is characterised by three distinct regions. The first region between delta pressures zero and P$_1$ is flat, or horizontal, and has a value of S$_1$. The second region between delta pressures P$_1$ and P$_2$ is linear and is characterised by a slope of greater than zero. The third region of delta pressures greater than P$_2$ is parabolic.

In one embodiment, apparatus 200 provides four different modes of regulating cuff pressure. However, each of the four modes uses a controller function that is characterised by the curve shown in FIG. 13.

In all four modes, the parabolic region of the controller curve is described by the following quadratic Equation 7. So, the number of steps per second taken by the motor 247, when the delta pressure is in the parabolic region, is equal to the square of the delta pressure times a constant. One preferred value for the constant K is 250.

$$\text{Steps} = (\text{delta pressure})^2 * K \quad \text{(Equation 7)}$$

In each of the four modes, the linear region of the curve shown in FIG. 13 is described by the following Equation 8. The linear region of mode zero, the mode that provides the slowest form of regulation, is characterized by a slope (of Equation 8) that is equal to 0.5. The linear region of mode one is characterized by a slope that is equal to 1.0. The linear region of mode two is characterized by a slope that is equal to 2.0. The linear region of mode three, the mode that provides the fastest form of regulation, is characterized by a slope that is equal to 4.0.

$$\text{Steps} = (\text{delta pressure}) * \text{slope} \quad \text{(Equation 8)}$$

In all four modes, the value S$_1$ (i.e., the height of the flat region) is equal to ten cm H$_2$O.

In all four modes, the value of point P$_1$ (as shown in FIG. 13) is determined by the intersection of the linear and flat regions. That is, the value of P$_1$ is the value of delta pressure for which the linear Equation 8 yields a number of steps per second equal to S$_1$. Similarly, in all four modes, the value of point P$_2$ is determined by the intersection of the linear and parabolic regions. That is, the value of P$_2$ is the value of delta pressure for which the linear Equation 8 yields a number of steps per second equal to the number yielded by the quadratic Equation 7.

In mode zero, P$_1$ equals about 1.0 and P$_2$ equals about 6.0. In mode one, P$_1$ equals about 0.5 and P$_2$ equals about 12.0. In mode two, P$_1$ equals about 0.22 and P$_2$ equals about 24.5. In mode three, P$_1$ equals about 0.12. In mode three, the parabolic region is almost never used.

The above-described four modes provide four different ways in which apparatus 200 may regulate the cuff pressure. It will be appreciated that other modes could also be defined as well. The purpose of defining different modes is to allow apparatus 200 to act in different ways that are suitable for different situations. For example, mode zero, the slowest mode of regulation, is appropriate when the patient is deeply anesthetized. As discussed above, apparatus 200 uses measured changes in cuff pressure to estimate the anesthetic state of a patient. Accordingly, when apparatus 200 is performing its estimating function (if apparatus is also simultaneously performing its regulating function), it is desirable for apparatus 200 to provide only minimal adjustments to cuff pressure so that all measured changes in cuff pressure are caused by action of the patient (and are not caused by apparatus 200). Mode zero generally provides only very minor adjustments to cuff pressure and therefore interferes only minimally with the estimating function of apparatus 200.

Mode one provides faster regulation than mode zero. However, mode one may also be used when apparatus 200 is providing its estimating function, and especially if a larger size LMA is being used (e.g., sizes 5 or 6). Since more air must be pumped into or out of larger size LMAs to affect their cuff pressure, it is appropriate to use a faster mode of regulation when larger size LMAs are being used.

Mode two provides even faster pressure regulation and is appropriate for use with lightly anesthetized patients that have active swallowing reflexes.

Mode three provides the fastest regulation. This mode is appropriate when apparatus 200 is not providing its estimating function and the only goal for apparatus 200 is to maintain a constant pressure in the LMA cuff.

It should be noted that apparatus 200 can monitor cuff pressure without also regulating cuff pressure. Accordingly, the estimating function (e.g., activating alarms and calculating patient activity) of apparatus 200 may be performed whether or not apparatus 200 is actively regulating cuff pressure. Also, if apparatus 200 is regulating cuff pressure, apparatus 200 may also perform its estimating function regardless of which of the regulating modes is being used. However, the estimating function is most likely to have the highest accuracy if one of the slower modes of regulation (e.g., mode zero) is being used, or if no regulation is being used at all. Finally, apparatus 200 may also perform its regulating function (i.e., maintain cuff pressure at the set point) without simultaneously performing its estimating function.

As generally described above, the most common use of LMAs is during surgical procedures. Normally, the LMA is inserted into the patient shortly before the beginning of surgery and is removed shortly after the surgery is completed. However, LMAs may also be used during long term, non-surgically related, stays in the hospital. For example, it can be advantageous to insert LMAs in patients that are in an intensive care unit (ICU) and to leave the LMAs in the patients for prolonged periods of time. Apparatus 200 may also usefully (1) regulate the cuff pressure of LMAs that are inserted in such patients and (2) estimate or monitor the state of such patents.

When an LMA remains in a patient for a long period of time, it is important to allow the patient to swallow comfortably. During swallowing, the pharynx contracts and thereby reduces the available space for the inflated LMA cuff. Accordingly, swallowing can be very uncomfortable or painful for the patient unless air is withdrawn from the cuff while the patient is swallowing. Also, the cuff pressure will rise dramatically during swallowing unless air is quickly removed from the cuff. The above described fast modes of pressure regulation (e.g., modes two or three) are fast enough to permit relatively comfortable swallowing. That is, when apparatus 200 is providing mode two or three regulation, and a patient swallows, the apparatus withdraws air from the cuff sufficiently fast to maintain the cuff pressure near the set point during swallowing and quickly moves air back into the cuff after swallowing is complete. From the patient's point of view, swallowing is relatively comfortable and they experience a softly compliant object (i.e., a collapsing LMA cuff) in their throat as opposed to a rigid object (i.e., a fully inflated LMA cuff). Also, by quickly reacting to the cuff pressure changes associated with swallowing, apparatus 200 allows the LMA to remain in a stable position within the patient for long periods of time.

In addition to regulating cuff pressure, apparatus 200 can provide an estimating function for patients in which LMAs have been inserted for long periods of time. The estimating function of apparatus 200 has been principally described above in connection with patients that have been anesthetized and are receiving IPPV. However, even if a patient is not receiving IPPV and is instead breathing spontaneously, the cuff pressure will tend to oscillate in a manner similar to that described above. That is, during spontaneous breathing, the cuff pressure tends to rise during inhalation and to fall during exhalation. The changes in cuff pressure caused by spontaneous breathing can be monitored in exactly the same way as the changes in cuff pressure caused by IPPV, and apparatus 200 can provide an indication or an alarm if the deviations in cuff pressure exceed a normal range. Such alarms can alert the staff of impending return of consciousness in time for them to prevent the patient experiencing significant distress. It will be appreciated that such monitoring of patients in an ICU can be very useful.

Since certain changes may be made in the above apparatus without departing from the scope of the invention herein involved, it is intended that all matter contained in the above description or shown in the accompanying drawing shall be interpreted in an illustrative and not a limiting sense. For example, the above described methods of operating the alarms analyze the cuff pressure relative to a mean value. In other embodiments, the calculations could be referenced to the set point instead of the mean value. As another example, apparatus 200 has been described as working with LMAs, however, apparatus 200 could be used in conjunction with any device in which an inflatable cuff, or balloon, is positioned in a patient's pharynx.

What is claimed is:

1. A method for monitoring a patient, the method comprising:
   positioning an inflated structure in the patient's upper airway between the patient's mouth and the patient's glottic opening;
   monitoring a pressure within the inflated structure over time, the pressure being indicative of a tone of muscles in the patient's larynx or pharynx;
   computing a value according to a function of changes in the pressure over time; and
   activating an alarm if the value departs from a predetermined range.

2. A method according to claim 1, further including activating the alarm when the pressure drops below a selected level.

3. A method according to claim 1, including positioning the inflated structure in the patient's pharynx.

4. A method according to claim 1, wherein the inflated structure comprises a cuff of a laryngeal mask airway device.

5. A method according to claim 1, wherein the inflated structure is inflated by an amount less than required to stretch walls of the structure.

6. A method according to claim 1, wherein the inflated structure is inflated by an amount sufficient to cause the structure to push against the patient's pharyngeal walls.

7. The method of claim 1, wherein computing the value comprises the step of calculating a mean of the pressure over a selected time interval.

8. The method of claim 1, wherein computing the value comprises calculating the difference between a mean of the pressure over a first time interval and a mean of the pressure over a second time interval, the first time interval being shorter than the second time interval.

9. The method of claim 8, wherein the first time interval occurs within the second time interval.

10. A method for monitoring a patient, the method comprising:

positioning an inflated structure in the patient's upper airway between the patient's mouth and the patient's glottic opening;

measuring a pressure within the inflated structure over time, the pressure being indicative of a tone of muscles in the patient's larynx or pharynx;

computing a value according to a function of changes in the pressure over time; and generating a signal if the value departs from a predetermined range.

11. A method according to claim 10, further comprising activating an alarm when the signal exceeds a threshold.

12. A method according to claim 10, the signal being representative of a level of awareness of the patient.

13. A method according to claim 10, further including monitoring a condition of the patient associated with changes in tone of the muscles in the patient's larynx or pharynx.

14. A method according to claim 13, wherein the condition of the patient is at least one of a tone of the pharyngeal constrictor muscles, a depth of anesthesia, and a level of awareness.

15. A method according to claim 10, wherein the pressure changes in response to changes in tone of muscles in the patient's hypopharynx.

* * * * *